United States Patent [19]
Calverley et al.

[11] Patent Number: 5,374,629
[45] Date of Patent: Dec. 20, 1994

[54] VITAMIN D ANALOGUES

[75] Inventors: Martin J. Calverley, Herlev; Gunnar Grue-Sørensen, Ølstykke; Ernst T. Binderup, Tåstrup, all of Denmark

[73] Assignee: Leo Pharmaceutical Products Ltd. A/S Lovens Kemiske Fabrik Produktionsaktieselskab, Ballerup, Denmark

[21] Appl. No.: 910,025
[22] PCT Filed: Mar. 22, 1991
[86] PCT No.: PCT/DK91/00091
  § 371 Date: Jul. 23, 1992
  § 102(e) Date: Jul. 23, 1992
[87] PCT Pub. No.: WO91/15475
  PCT Pub. Date: Oct. 17, 1991

[30] Foreign Application Priority Data

Mar. 30, 1990 [GB] United Kingdom ............... 9007236

[51] Int. Cl.$^5$ .................................... C07C 401/00
[52] U.S. Cl. .................................... 514/167; 552/653
[58] Field of Search .................. 552/653; 514/167

[56] References Cited

FOREIGN PATENT DOCUMENTS

| | | |
|---|---|---|
| 78704 | 5/1983 | European Pat. Off. . |
| 230600 | 8/1987 | European Pat. Off. . |
| 296800 | 12/1988 | European Pat. Off. . |
| 377743 | 7/1990 | European Pat. Off. . |

OTHER PUBLICATIONS

Neef, et al., *Tetrahedron Letters*, 32(38), 1991, pp. 5073-5076.
Kubodera, et al., *Chem Pharm Bull*, 39(12), 1991, pp. 3221-3224.
WO, A, 8910353 Deluca et al, Nov. 1989, See claim 1.
Proc. Workshop on Vitamin D, 1988, N. Ikekawa: "Chemical synthesis of vitamin D analogs with selective biological activities", pp. 25-33, see p. 30, compound 20.
Bioorganic Chemistry, vol. 17, No. 3, 1989, Eguchi et al, "Synthesis and biological activities of 22-hydroxy and 22-methoxy derivatives of 1, 25-dihydroxyvitamin D3: Importance of side chain conformation for biological activities", pp. 294-307 see the whole document.
Chemical Abstracts, vol. 114, No. 17, 1991, see p. 820, abstract No. 164627h & JP, A. 02215766, Aug. 1990.
Norman et al., Bioochem. Biophys. Res. Commun., 189, (1992), 1450-1456.
Lowe et al., Vitamin D-Mediated Gene Expression, Critical Reviews in Eukaryotic Gene Expression, 2, (1992) 65-109.
Calverley et al., Vitamin D in Antimumor Steroids, ed. by R. T. Blickenstaff, Academic Press, San Diego, (1992) 193-270.
DeLuca, Ann. N Y Acad. Sci., 669, (1992) 59-69.
M. Bower et al., Topical Calcipotriol Treatment In Advanced Breast Cancer, Lancet, 337, (1991 701-702.
Oikawa et al., Anti-Cancer Drugs, 2, (1991) 475-480.
K. W. Colston et al., Biochem. Pharmacol., 44, (1992) 693-702.
A. Szabo et al., Kidney Int., 35, (1989) 1049-1056.
A. J. Brown et al., J. Clin. Invest., 84, (1989) 728-732.
Binderup, Biochem. Pharmacol., 43, (1992) 1885-1892.
Binderup, Biochem. Pharmacol., 37, (1988) 889-895.
Binderup et al., Biochem. Pharmacol., 42, (1991) 1569-1575.

*Primary Examiner*—Johann Richter
*Assistant Examiner*—Kimberly J. Kestler
*Attorney, Agent, or Firm*—Cushman, Darby & Cushman

[57] ABSTRACT

The invention relates to compounds of formula I

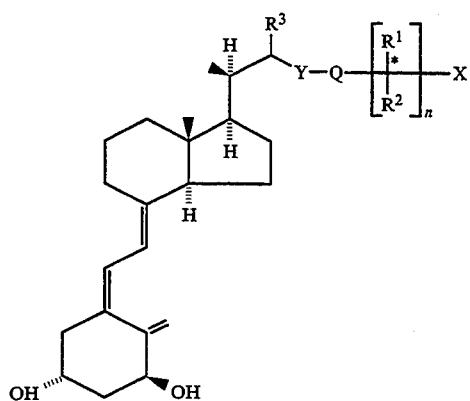

in which formula X is hydrogen or hydroxy; Y is oxygen, sulphur, or oxidized sulfur (S(O) or S(O$_2$)); $R^1$ and $R^2$, which may be the same or different, stand for hydrogen or $C_1$-$C_6$ hydrocarbyl, or $R^1$ and $R^2$, taken together with the carbon atom (starred in formula I) bearing the group X, form a $C_3$-$C_8$ carbocyclic ring; Q is a $C_1$-$C_8$ hydrocarbylene diradical. $R^3$ is hydrogen or $C_1$-$C_6$ hydrocarbyl. $R^1$, $R^2$ and/or Q, may be optionally substituted with one or more deuterium or fluorine atoms; n is 0 or 1. The present compounds show antiinflammatory and immunomodulating effects as well as a strong activity in inducing cell differentiation and inhibiting undesirable proliferation of certain cancer and skin cells.

6 Claims, No Drawings

VITAMIN D ANALOGUES

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism and a number of disease states including diabetes mellitus, hypertension, acne, alopecia, skin ageing, imbalance in the immune system, inflammatory diseases such as rheumatoid arthritis and asthma as well as diseases characterized by abnormal cell differentiation and/or cell proliferation such as e.g. psoriasis and cancer.

The compounds of the present invention are represented by the general formula I

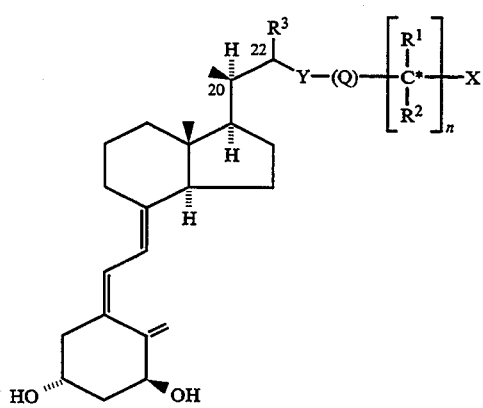

in which formula X is hydrogen or hydroxy; Y is oxygen or sulphur or oxidized sulphur (S(O) or S(O$_2$)); R$^1$ and R$^2$, which may be the same or different, stand for hydrogen or C$_1$–C$_6$ hydrocarbyl; or R$^1$ and R$^2$ taken together with the carbon atom (starred in formula I) bearing the group X, can form a C$_3$–C$_8$ carbocyclic ring; Q is a C$_1$–C$_8$ hydrocarbylene diradical. R$^3$ is hydrogen or C$_1$–C$_6$ hydrocarbyl. R$^1$, R$^2$ and/or Q may be optionally substituted with one or more deuterium or fluorine atoms. n is 0 or 1.

In the context of this invention, the expression hydrocarbyl radical (hydrocarbylene diradical) indicates the residue after removal of 1 (2) hydrogen atom(s) from a straight, branched or cyclic saturated or unsaturated hydrocarbon.

Examples of R$^1$ and R$^2$ when taken separately include (apart from hydrogen), but are not limited to, methyl, trifluoromethyl, ethyl, vinyl, normal-, iso- and cyclopropyl, and 1-methylvinyl.

Examples of R$^1$ and R$^2$ when taken together include di-, tri-, tetra- and penta-methylene.

Examples of Q include methylene, di-, tri- and tetra-methylene, —CH$_2$—CH=CH—, —CH$_2$—C≡C—, phenylene (C$_6$H$_4$; ortho, meta, para), —CH$_2$—(C$_6$H$_4$)-(ortho, meta, para), and —(C$_6$H$_4$)—CH$_2$ (ortho, meta, para), and Examples of R$^3$ include (apart from hydrogen) methyl, normal-butyl and phenyl.

As can be seen from formula I, depending on the meanings of R$^1$, R$^2$, R$^3$ and X the compounds of the invention can comprise several diastereoisomeric forms (e.g. R or S configuration at the starred carbon atom). The invention covers all these diastereoisomers in pure form and also mixtures of diastereoisomers. In addition, derivatives of I in which one or more of the hydroxy groups are masked as groups which can be reconverted to hydroxy groups in vivo are also within the scope of the invention ("bioreversible derivatives or prodrugs of I").

The term "bioreversible derivatives or prodrugs of I" includes, but is not limited to, derivatives of the compounds of formula I in which one or more hydroxy groups have been transformed into —O-acyl or —O-glycosyl groups, or a phosphate ester, such masked groups being hydrolyzable in vivo.

The compounds I in which X is hydrogen are another type of prodrug. These compounds are relatively inactive in vitro, but are converted to active compounds of formula I by enzymatic hydroxylation after administration to the patient.

It has recently been shown that 1α,25-dihydroxyvitamin D$_3$ (1,25(OH)$_2$D$_3$) influences the effects and/or production of interleukins, indicating the potential use of this compound in the treatment of diseases characterized by a dysfunction of the immune system, e.g. autoimmune diseases and rejection of transplants. In addition, other conditions characterized by an abnormal interleukin production, e.g. inflammatory diseases such as rheumatoid arthritis may be treated with 1,25(OH)$_2$D$_3$.

It has also been shown that 1,25(OH)$_2$D$_3$ is able to stimulate the differentiation of cells and inhibit excessive cell proliferation, and it has been suggested that this compound might be useful in the treatment of diseases characterized by abnormal cell proliferation and/or cell differentiation such as cancer and psoriasis.

Also, the use of 1,25(OH)$_2$D$_3$ for the treatment of hypertension and diabetes mellitus has been suggested.

However, the therapeutic possibilities in such indications of 1,25 (OH)$_2$D$_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, cancer or immune diseases which may require continuous administration of the drug in relatively high doses.

A number of oxa- and thia-analogues of vitamin D$_3$ are known. 1α,25-dihydroxy-20-oxa-21-norvitamin D$_3$ and 1α-hydroxy-20-oxa-21-norvitamin D$_3$ are described in N. Kubodera et al, Chem. Pharm. Bull., 34, 2286 (1986), 1α25-dihydroxy-22-oxavitamin D$_3$ and 25-hydroxy-22-oxavitamin D$_3$ are described in E. Murayama et al, Chem. Pharm. Bull., 34, 4410 (1986), J. Abe et al, FEBS LETTERS, 226, 58 (1987) and European Patent Application, publication number 184 112, and 1α,25-dihydroxy-23-oxavitamin D$_3$ and 1α,25-dihydroxy-23-thiavitamin D$_3$ are described in European Patent Application, publication number 78704.

Some of these compounds may have advantages over 1,25(OH)$_2$D$_3$. Thus 1α,25-dihydroxy-22-oxavitamin D$_3$ is reported to have a high activity as inducer of differentiation in a cancer cell line, while having reduced calcium metabolism effects relative to 1,25(OH)$_2$D$_3$.

Although no data are published for the known 23-oxa and 23-thia analogues, we have found that these compounds show on the other hand only poor activity in the cell differentiation test.

The compounds of the present invention differ structurally from all the above mentioned oxa and thia compounds in that they possess R-configuration at the 20-position.

The usefulness of a vitamin D analogue in the above mentioned indications is dependent not only upon a high activity demonstrated in an in vitro cell differentiation test, but also upon the fate of the compound in the organism.

It has now been found that the compounds of the present invention show favourable selectivity with respect to their effects on cell differentiation in vitro and their calcemic effects in vivo, and at the same time show high bioavailability as well as chemical and metabolic stability.

The selectivity of the compounds is illustrated by the fact that while the concentration needed to induce cell differentiation in a human monocytic rumour cell line is the same as or considerably lower than that needed of $1,25(OH)_2D_3$ to give the same effect, in vivo in rats the compounds are less active than $1,25(OH)_2D_3$ in inducing hypercalciuria and hypercalcemia.

This renders the compounds of the invention especially suited for both local and systemic treatment and prophylaxis of human and veterinary disorders which are characterized by abnormal cell proliferation and/or cell differentiation, such as certain dermatological disorders including psoriasis and certain cancer forms, e.g. leukemia and myelofibrosis. The compounds can also inhibit metastasis of these cancers. The compounds are also useful for treatment and prophylaxis of diseases characterized by an imbalance in the immune system, e.g. autoimmune diseases, or AIDS, and to obtain desired immunosuppression as in transplantation procedures, as well as treatment of acne, diabetes mellitus and hypertension and inflammatory diseases, such as rheumatoid arthritis and asthma. As the compounds of this invention may promote the differentiation of the hair follicle cells, these compounds may be used in the treatment of alopecia. In view of the relatively low calcaemic effects, these compounds may also be used in the treatment of hyperparathyroidism.

The compounds of formula I in which Y=O or S may conveniently be prepared from the vitamin D-derivative 1 (Tetrahedron, 4.3, 4609 (1987)) for example by the routes outlined in Scheme 1. O-Alkylation of I or S-alkylation of III to give IV is achieved by treatment under basic conditions with a side chain building block of general formula Z—R, in which Z is a leaving group such as a halogen (Cl, Br or I) or p-toluenesulphonyloxy or trifluoromethanesulphonyloxy, and R is —(Q)—[C(R$^1$)(R$^2$)]$_n$X or optionally a radical which can be converted to this at any convenient later stage (or over several stages). Thus R in compounds IV, V, VI and VII does not necessarily have the same meaning along a particular synthetic sequence. The conversion of R to —(Q)—[C(R$^1$)(R$^2$)]$_n$X may well involve several steps and possibly involve a temporary protection of the sensitive triene system of the molecule. An alternative to this route involves treatment of the intermediate II (Z is a leaving group as described above) under basic conditions with a side chain building block HY—R, in which Y is oxygen or sulphur and R is as described above, to give the intermediate IV. Apart from any necessary modification within the side chain (R), the conversion of IV to I involves a photoisomerisation step and a desilylation step, analogous to the steps used in the last stages of the synthesis of other vitamin D analogues (see European patent No. 0 227 826).

It may be convenient to change the order of the alkylation reaction (d or e) and the photoisomerisation reaction (g), in which case the (5Z)-isomer of I, II, or III is a key intermediate.

The side chain building blocks, RZ, are either known compounds (several are described in international patent application PCT/DK89/00079) or may be prepared analogously to those described in PCT/DK89/00079. The R is typically —(Q)—[C(R$^1$)(R$^2$)]$_n$X$^1$ in which X$^1$ is a protected OH group, e.g. tetrahydropyranyloxy or trialkylsilyloxy. (Any such THP ethers RZ, which are not described in PCT/DK89/00079, are readily prepared from the corresponding alcohol).

The side chain building block HY—R are also known compounds or may be prepared by methods analogous to those used to prepare such known compounds.

As schematized above, at least for the 23-thia compounds the route does not exclude deferring the alkylation of a 23-thiol even as far as the last step (e.g. VII. R=H→I).

The compounds of formula I in which Q=S(O) or S(O$_2$) may conveniently be prepared via oxidation of a corresponding compound IV, V, VI, VII or I, in which Q=S, for example with hydrogen peroxide and sodium tungstate in aqueous methanol. (The diastereoisomeric sulfoxides (Q=S(O)) may be separated chromatographically).

The following standard abbreviations are used throughout this disclosure: Me=methyl; Et=ethyl; Pr$^n$=n-propyl; Pr$^i$=isopropyl; Bu$^t$=tert-butyl; THP=tetrahydro-4H-pyran-2-yl; THF=tetrahydrofuran: Ts=p-toluenesulphonyl; TBA=tetra-(n-butyl)-ammonium; DMF=dimethylformamide.

Scheme 1

-continued
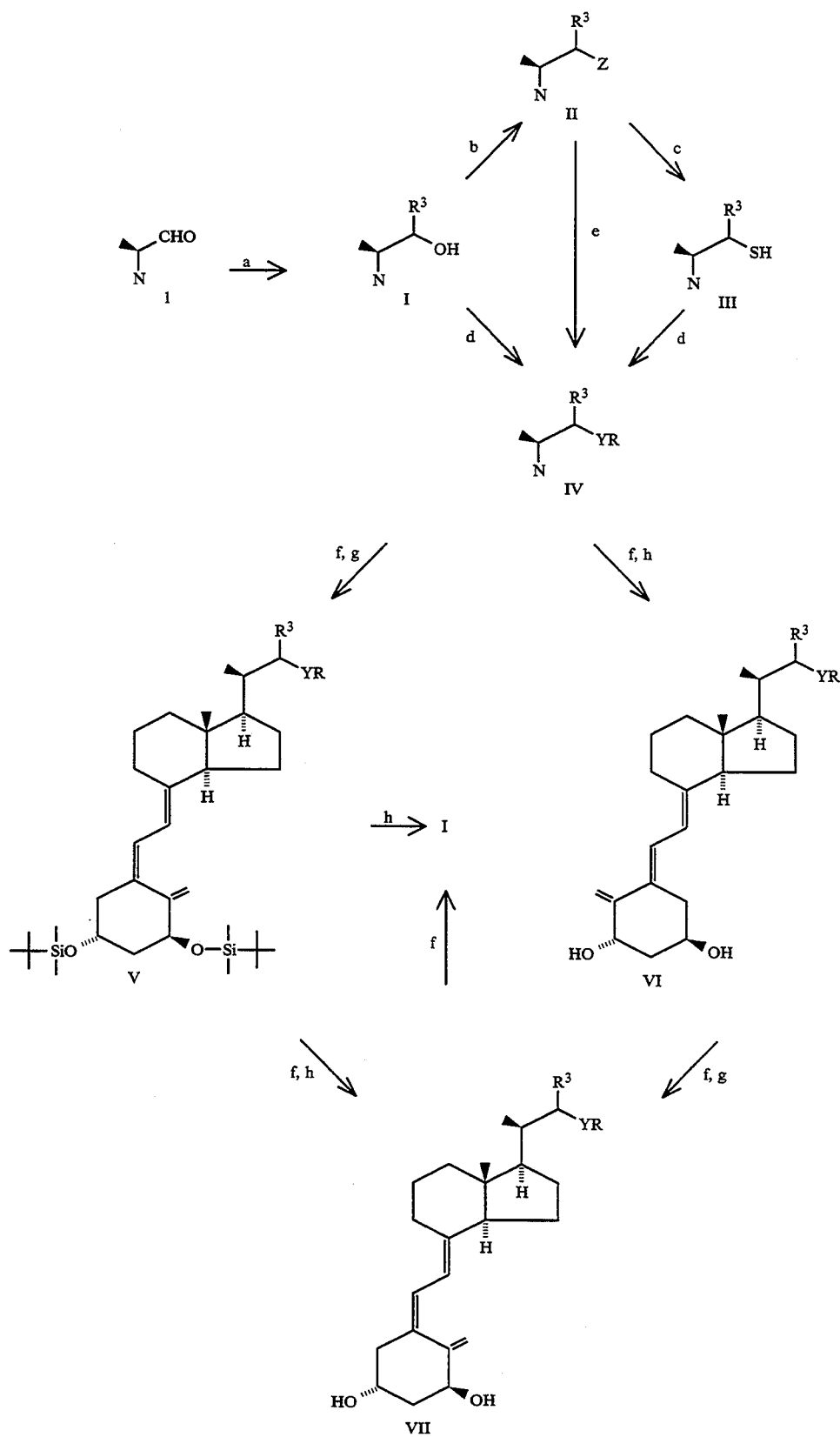

-continued

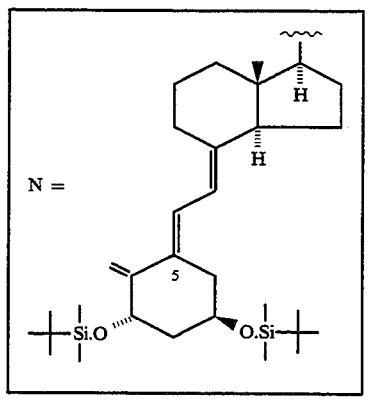

Notes to Scheme 1 a) Reaction with formal source of $R^{3\ominus}$ (e.g. reduction with $NaBH_4$ for $R^3$ = H or reaction with $R^3Li$ for $R^3$ = hydrocarbyl); optional separation of diastereoisomers for $R^3$ = hydrocarbyl (e.g. by chromatography).
b) Conversion of OH to a leaving group (e.g. by tosylation for Z = OTs).
c) (i) Nucleophilic substitution with thioacetate, (ii) basic hydrolysis.
d) Alkylation with the side chain building block R—Z in the presence of base (e.g. KOH, $KOBu^t$ or KH), with or without catalyst (e.g. 18-Crown-6) in solvent (e.g. THF).
e) Reaction with the side chain building block R—YH in the presence of base (e.g. NaH) in solvent, e.g. DMF.
f) Optional functional group modification in the side chain.
g) Isomerisation with $h\nu$ - triplet sensitizer, e.g. anthracene.
h) Deprotection with $TBA^+F^-$ or HF.

It should be noted that although the shown intermediates may have hydroxyl groups protected as tert-butyldimethylsilyl ethers, the scope of the invention does not exclude the use of alternative hydroxyl protecting groups well known in the art (such as those described in T. W. Greene, "Protective groups in organic synthesis", Wiley, N.Y., 1981), together with alternative reactions for deprotection.

The present compounds are intended for use in pharmaceutical compounds which are useful in the treatment of human and veterinarY disorders as described above. The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enternally and this is the preferred route of administration in the treatment of systemci disorders. In the treatment of dematololgical disorders like psoriasis, topical or enteral are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including topical application to the eye, include liquid or semi-liquid preparations such as liniments, lotions, applicants, oil-in-water or water-in-oil emulsions such as creams, ointments or pastes, or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100 μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and flourinated $C_1$–$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 μg, preferably from 0.2–25 μg, of a compound of formula I are administered. In the topical treatment of dermatological disorders, ointments, creams or lotions containing from 0.1–500 μg/g, and preferably from 1–100 μg/g, of a compound of formula I are administered. The oral compositions are formulated, preferably as tablets, capsules, or drops, containing from 0.05–50 μg, preferably from 0.1–1.25 μg, of a compound of formula I, per dosage unit.

The invention will now be further described in the following non-limiting Preparations and Examples:

PREPARATIONS AND EXAMPLES

General

The exemplified compounds I are listed in Table 1. The intermediates of Scheme I referred to in the Preparations are to be identified by numbers with the corresponding formulae in Table 2. These are used to illustrate typical syntheses of the exemplified compounds I.

For nuclear magnetic resonance spectra (300 MHz) chemical shift values (δ) are quoted in ppm for deuteriochloroform solutions (except where otherwise stated) relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. If not specified, % means v/v %. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

TABLE 1

Examples of Compounds of formula I (n = 1, except for compounds 140, 141, 147, 148, 149, 152) (Details are provided for compounds where an Example Number is given; the other compounds may be prepared using analogous reaction sequences from known starting materials)

| Compound Number | Example Number | $R^3$ | Y | Q | $R^1$ | $R^2$ | X |
| --- | --- | --- | --- | --- | --- | --- | --- |
| 101 |  | H | O | $CH_2$ | Me | Me | OH |
| 102 | 1 | H | O | $(CH_2)_2$ | Me | Me | OH |
| 103 | 16 | H | O | $(CH_2)_2$ | Et | Et | OH |
| 104 |  | H | O | $(CH_2)_3$ | H | H | OH |
| 105 |  | H | O | $(CH_2)_3$ | Me | Me | H |

TABLE 1-continued

Examples of Compounds of formula I (n = 1, except for compounds 140, 141, 147, 148, 149, 152) (Details are provided for compounds where an Example Number is given; the other compounds may be prepared using analogous reaction sequences from known starting materials)

| Compound Number | Example Number | $R^3$ | Y | Q | $R^1$ | $R^2$ | X |
|---|---|---|---|---|---|---|---|
| 106 | 2 | H | O | $(CH_2)_3$ | Me | Me | OH |
| 107[Θ] | 15 | H | O | $CH_2$—CH=CH— | Me | Me | OH |
| 108 | 3 | H | O | $CH_2$—C≡C— | Me | Me | OH |
| 109 | 26 | H | O | $CH_2$—C≡C— | $CF_3$ | $CF_3$ | OH |
| 110 | | H | O | $CH_2$—C≡C— | —$(CH_2)_5$— | | OH |
| 111 | 10 | H | O | meta-$C_6H_4$ | Me | Me | OH |
| 112[*,Θ] | | Me | O | $CH_2$—CH=CH | Me | Me | OH |
| 113[*,Θ] | | Me | O | $CH_2$—CH=CH | Me | Me | OH |
| 114[**] | | H | S | $CH_2$ | H | Cyclo-Pr | OH |
| 115[++] | | H | S | $CH_2$ | H | Cyclo-Pr | OH |
| 116 | 4 | H | S | $CH_2$ | Me | Me | OH |
| 117 | 5 | H | S | $(CH_2)_2$ | Me | Me | OH |
| 118[o] | | H | S(O) | $(CH_2)_2$ | Me | Me | OH |
| 119[oo] | | H | S(O) | $(CH_2)_2$ | Me | Me | OH |
| 120 | | H | $S(O)_2$ | $(CH_2)_2$ | Me | Me | OH |
| 121 | 6 | H | S | $(CH_2)_2$ | Et | Et | OH |
| 122[*] | | Me | S | $(CH_2)_2$ | Me | Me | OH |
| 123[+] | | Me | S | $(CH_2)_2$ | Me | Me | OH |
| 124[*] | | Me | S | $(CH_2)_2$ | Et | Et | OH |
| 125[+] | | Me | S | $(CH_2)_2$ | Et | Et | OH |
| 126 | 7 | H | O | $(CH_2)_2$ | Me | Me | OH |
| 127 | 8 | H | O | ortho-$C_6H_4$ | Me | Me | OH |
| 128 | 9 | H | O | ortho-$C_6H_4$ | Et | Et | OH |
| 129 | 11 | H | O | meta-$C_6H_4$ | Et | Et | OH |
| 130 | 12 | H | O | para-$C_6H_4$ | Me | Me | OH |
| 131 | 13 | H | O | para-$C_6H_4$ | Et | Et | OH |
| 132 | 14 | H | O | meta-$C_6H_4$ | H | H | OH |
| 133[§§] | 17 | H | S(O) | $(CH_2)_2$ | Et | Et | OH |
| 134[§§§] | 18 | H | S(O) | $(CH_2)_2$ | Et | Et | OH |
| 135 | 19 | H | $S(O_2)$ | $(CH_2)_2$ | Et | Et | OH |
| 136 | 20 | H | S | $(CH_2)_3$ | Me | Me | OH |
| 137 | 21 | H | S | meta-$C_6H_4$ | H | H | OH |
| 138 | 22 | H | S | meta-$C_6H_4$ | Me | Me | OH |
| 139 | 23 | H | O | $CH_2$—C≡C— | Et | Et | OH |
| 140[§] | 24 | H | O | ortho-$C_6H_4$ | — | — | OH |
| 141[§] | 25 | H | O | meta-$C_6H_4$ | — | — | OH |
| 142 | | H | S | ortho-$C_6H_4$ | Me | Me | OH |
| 143 | | H | S | ortho-$C_6H_4$ | Et | Et | OH |
| 144 | | H | S | meta-$C_6H_4$ | Et | Et | OH |
| 145 | | H | S | para-$C_6H_4$ | Me | Me | OH |
| 146 | | H | S | para-$C_6H_4$ | Et | Et | OH |
| 147[§] | | H | S | ortho-$C_6H_4$ | — | — | OH |
| 148[§] | | H | S | meta-$C_6H_4$ | — | — | OH |
| 149[§] | | H | S | para-$C_6H_4$ | — | — | OH |
| 150 | | H | S | $CH_2$ | Et | Et | OH |
| 151 | | H | S | $(CH_2)_3$ | Et | Et | OH |
| 152[§] | | H | O | para-$C_6H_4$ | — | — | OH |
| 153 | 27 | H | O | $(CH_2)_2CF_2$ | Me | Me | OH |
| 154[ΘΘ] | | H | O | $CH_2$—CH=CH— | Me | Me | OH |

[Θ](E) configuration of double bond in Q
[ΘΘ](Z) configuration of double bond in Q
[*]22(S)-form
[+]22(R)-form
[**](S) configuration at starred carbon atom
[++](R) configuration at starred carbon atom
[o](S) configuration of sulphoxide
[oo](R) configuration of sulphoxide
[§]n = 0
[§§]Isomer with compound 134
[§§§]Isomer with compound 133

TABLE 2

| Compound Number | Preparation Number | Type (See Scheme 1) | Formula | |
|---|---|---|---|---|
| | | | $R^3$ | YR or Z |
| 2 | 1 | I | H | — |
| 3 | 2 | I | Me* | — |
| 4 | 2 | I | Me+ | — |
| 5 | 3 | II | H | OTs |
| 6 | 4, 62 | IV | H | O—$CH_2$—CH=$CMe_2$ |
| 7 | 7 | IV | H | O—$(CH_2)_2$—C(OH)$Me_2$ |
| 8 | 5 | IV | H | O—$(CH_2)_3$—C(OSi$Me_3$)$Me_2$ |
| 9 | 6 | IV | H | O—$CH_2$—C≡C—H |
| 10 | 8 | IV | H | O—$CH_2$—C≡C—C(OH)$Me_2$ |

TABLE 2-continued

| Compound Number | Preparation Number | Type (See Scheme 1) | $R^3$ | YR or Z |
|---|---|---|---|---|
| 11 | 9 | IV | H | O—CH$_2$—C≡C—C(OH)(CH$_2$)$_4$CH$_2$ (cyclic) |
| 12 | 10 | IV | H | O—CH$_2$—C≡C—C(OH)(CF$_3$)$_2$ |
| 13 | 11 | IV | H | S—CH$_2$—C(OH)Me$_2$ |
| 14 | 12 | IV | H | S—(CH$_2$)$_2$—C(OH)Me$_2$ |
| 15 | 13 | IV | H | S—(CH$_2$)$_2$—C(OH)Et$_2$ |
| 16 | 14 | V | H | O—(CH$_2$)$_2$—C(OH)Me$_2$ |
| 17 | 15 | V | H | O—(CH$_2$)$_3$—C(OSiMe$_3$)Me$_2$ |
| 18 | 16 | V | H | S—CH$_2$—C(OH)Me$_2$ |
| 19 | 17 | V | H | S—(CH$_2$)$_2$—C(OH)Me$_2$ |
| 20 | 18 | V | H | S—(CH$_2$)$_2$—C(OH)Et$_2$ |
| 21 | 19 | V | H | O—CH$_2$—C≡C—C(OH)Me$_2$ |
| 22 | 20 | IV | H | O—CH$_2$—CH=CEt$_2$ |
| 23$^\theta$ | 21 | IV | H | O—CH$_2$—CH=CH—C(OSiMe$_3$)Me$_2$ |
| 24 | 22 | IV | H | O—(CH$_2$)$_4$—C(OSiMe$_3$)Me$_2$ |
| 25 | 23 | IV | H | O-ortho-C$_6$H$_4$—C(OH)Me$_2$ |
| 26 | 24 | IV | H | O-ortho-C$_6$H$_4$—C(OH)Et$_2$ |
| 27 | 25 | IV | H | O-meta-C$_6$H$_4$—C(OH)Me$_2$ |
| 28 | 26 | IV | H | O-meta-C$_6$H$_4$—C(OH)Et$_2$ |
| 29 | 27 | IV | H | O-para-C$_6$H$_4$—C(OH)Me$_2$ |
| 30 | 28 | IV | H | O-para-C$_6$H$_4$—C(OH)Et$_2$ |
| 31 | 29 | IV | H | O-meta-C$_6$H$_4$—CH$_2$OH |
| 32 | 30 | V | H | O—(CH$_2$)$_4$—C(OSiMe$_3$)Me$_2$ |
| 33 | 31 | V | H | O-ortho-C$_6$H$_4$—C(OH)Me$_2$ |
| 34 | 32 | V | H | O-ortho-C$_6$H$_4$—C(OH)Et$_2$ |
| 35 | 33 | V | H | O-meta-C$_6$H$_4$—C(OH)Me$_2$ |
| 36 | 34 | V | H | O-meta-C$_6$H$_4$—C(OH)Et$_2$ |
| 37 | 35 | V | H | O-para-C$_6$H$_4$—C(OH)Me$_2$ |
| 38 | 36 | V | H | O-para-C$_6$H$_4$—C(OH)Et$_2$ |
| 39 | 37 | V | H | O-meta-C$_6$H$_4$—CH$_2$OH |
| 40$^\theta$ | 38 | V | H | O—CH$_2$—CH=CH—C(OSiMe$_3$)Me$_2$ |
| 41 | 39 | IV | H | O—(CH$_2$)$_2$—C(OH)Et$_2$ |
| 42 | 40 | V | H | O—(CH$_2$)$_2$—C(OH)Et$_2$ |
| 43** | 41 | IV | H | S(O)—(CH$_2$)$_2$—C(OH)Et$_2$ |
| 44*** | 41 | IV | H | S(O)—(CH$_2$)$_2$—C(OH)Et$_2$ |
| 45 | 42 | IV | H | S(O$_2$)—(CH$_2$)$_2$—C(OH)Et$_2$ |
| 46 | 43 | IV | H | S—(CH$_2$)$_3$—COOCH$_3$ |
| 47 | 44 | IV | H | S-meta-C$_6$H$_4$—COOH |
| 48 | 45 | IV | H | S-meta-C$_6$H$_4$—COOMe |
| 49 | 46 | IV | H | OCH$_2$—C≡C—C(OH)Et$_2$ |
| 50+++ | 47 | V | H | S(O)—(CH$_2$)$_2$—C(OH)Et$_2$ |
| 51++++ | 48 | V | H | S(O)—(CH$_2$)$_2$—C(OH)Et$_2$ |
| 52 | 49 | V | H | S(O$_2$)—(CH$_2$)$_2$—C(OH)Et$_2$ |
| 53 | 50 | V | H | S—(CH$_2$)$_3$—COOCH$_3$ |
| 54 | 51 | V | H | S-meta-C$_6$H$_4$—COOCH$_3$ |

TABLE 2-continued

| Compound Number | Preparation Number | Type (See Scheme 1) | R³ | YR or Z |
|---|---|---|---|---|
| 55 | 52 | V | H | $OCH_2C\equiv C-C(OH)Et_2$ |
| 56 | 53 | V | H | $S-(CH_2)_3-C(OH)Me_2$ |
| 57 | 54 | V | H | S-meta-$C_6H_4$-C(OH)Me$_2$ |
| 58 | 55 | V | H | S-meta-$C_6H_4$-CH$_2$OH |
| 59 | 56 | IV | H | O-ortho-$C_6H_4$-OH |
| 60 | 57 | IV | H | O-ortho-$C_6H_4$-OH |
| 61 | 58 | V | H | O-meta-$C_6H_4$-OH |
| 62 | 59 | V | H | O-meta-$C_6H_4$-OH |
| 63 | 60 | III | H | - |
| 64 | 61 | IV | H | $O-CH_2C\equiv C-C(OH)(CF_3)_2$ |
| 65 | 63 | IV | H | $O-(CH_2)_2CF_2-CMe_2-OCH(Me)OEt$ |
| 66 | 64 | V | H | $O-(CH_2)_2CF_2-CMe_2-OCH(Me)OEt$ |

º, *, +: See Table 1
** Isomer with Compound 44
*** Isomer with Compound 43
+++ Isomer with Compound 51
++++ Isomer with Compound 50

Preparation 1

1(S),3(R)-bis-tert-butyldimethylsilyloxy-20(R)-hydroxymethyl-9,10-secopregna-5(E),7(E),10(19)-triene (Compound 2)

A stirred, ice-cooled solution of the aldehyde 1 (5 g) in THF (20 ml) and ethanol (70 ml) was treated with sodium borohydride (0.35 g). After 10 minutes the reaction mixture was partitioned between ethylacetate and water, and the organic layer was washed with brine and dried. Concentration in vacuo gave the title compound, NMR: δ=0.05 (bs, 12H), 0.56 (s, 3H), 0.86 (s, 9H), 0.89 (s, 9H), 0.96 (d, 3H, J=7), 1.1-2.1 (m, 15H), 2.31 (bd, 1H), 2.55 (dd, 1H, J=14 and 5), 2.86 (bd, 1H), 3.48 (dd, 1H, J=10 and 7), 3.71 (dd, 1H, J=11 and 4), 4.21 (m, 1H), 4.52 (m, 1H), 4.93 (bs, 1H), 4.98 (bs, 1H), 5.82 (d, 1H, J=11.5), and 6.44 (d, 1H, J=11.5).

Preparation 2

Compounds 3 and 4

To a solution of Compound 1 (0.8 g) in dry THF (7 ml), cooled to −40° C. and stirred under N$_2$, was added dropwise a solution of methyl-lithium (1.5M in ether, 1.2 ml). After 15 minutes, ether (50 ml) was added and the reaction mixture was worked up. The residue was purified by chromatography (10% ethyl acetate in petroleum ether as eluant) to give the less polar isomer; NMR: δ=0.05 (m, 12H), 0.54 (s, 3H), 0.85 (d, 3H), 0.85 (s, 9H), 0.89 (s, 9H), 1.13 (d, 3H, J=6.4), 1.00-2.10 (m, 15H), 2.31 (bd, 1H), 2.54 (dd, 1H), 2.88 (bd, 1H), 4.06 (m, 1H), 4.21 (m, 1H), 4.52 (m, 1H), 4.93 (m, 1H), 4.98 (m, 1H), 5.82 (d, 1H, J=11.4), 6.44 (d, 1H, J=11.4), and the more polar isomer; NMR: δ=0.05 (m, 12H), 0.56 (s, 3H), 0.85 (d, 3H), 0.85 (s, 9H), 0.89 (s, 9H), 1.07 (d, 3H, J=6.3), 1.00-2.10 (m, 15H), 2.31 (bd, 1H), 2.54 (dd, 1H), 2.88 (bd, 1H), 4.10 (m, 1H), 4.21 (m, 1H), 4.52 (m, 1H), 4.93 (m, 1H), 4.98 (m, 1H), 5.82 (d, 1H, J=11.4), 6.44 (d, 1H, J=11.4).

Preparation 3

1(S),3(R)-bis-tert-butyldimethylsilyloxy-20(R)-p-toluenesulphonyloxymethyl-9,10-secopregna-5(E),-7(E),10(19)-triene (Compound 5)

Compound 2 (5 g) was dissolved in dichloromethane (25 ml) and pyridine (3 ml), and the solution was stirred and ice-cooled during the addition of p-toluenesulphonyl chloride (2.5 g). The reaction mixture was allowed to stand at 5° C. overnight before being partitioned between ethyl acetate and water. The organic layer was washed consecutively with saturated cupric sulphate solution (twice), water, 5% sodium hydrogen carbonate solution, and brine, and then dried and concentrated in vacuo. The residue was purified by chromatography (200 g silica gel; 5% ether in petroleum ether as eluant) to give the title compound, (m.p. 98°-100° C. from MeOH), NMR: δ=0.035 (s, 3H), 0.044 (s, 3H), 0.051 (s, 3H), 0.056 (s, 3H), 0.45 (s, 3H), 0.85 (s, 9H), 0.88 (s, 9H), 0.89 (d, 3H, J=6), 1.15-2.05 (m, 14H), 2.28 (bd, 1H), 2.44 (s, 3H), 2.52 (dd, 1H, J=14 and 5), 2.84 (bd, 1H), 3.81 (m, 1H), 4.11 (m, 1H), 4.20 (m, 1H), 4.51 (m, 1H), 4.93 (bs, 1H), 4.97 (bs, 1H), 5.79 (d, 1H, J=11), 6.42 (d, 1H, J=11), 7.33 (bd, 2H), 7.78 (bd, 2H).

General Procedure 1

O-alkylation of Compound I; (Preparations 4-6 and 20-21)

To a solution stirred under nitrogen of Compound I (ca. 1 mmol) in dry THF (10 ml) were added sequentially potassium tert-butoxide (0.4 g), 18-Crown-6 (80 mg) and the requisite alkylating agent. The mixture was stirred for 1 hour and then worked up (ether) to give a residue which was purified appropriately.

Preparation 4

Compound 6

Compound I: Compound 2.

Alkylating agent: 3,3-dimethylallyl bromide (0.3 g)

Method of purification: Direct crystallization from ether-methanol.

NMR: δ=0.05 (m, 12H), 0.55 (s, 3H), 0.86 (s, 9H), 0.89 (s, 9H), 0.95 (d, 3H, J=6.6), 1.66 (bs, 3H), 1.73 (bs, 3H), 1.20–2.10 (m, 14H), 2.31 (bd, 1H), 2.55 (dd, 1H), 2.87 (bd, 1H), 3.15 (dd, 1H), 3.50 (dd, 1H), 3.90 (m, 2H), 4.21 (m, 1H), 4.53 (m, 1H), 4.93 (m, 1H), 4.98 (m, 1H), 5.34 (m, 1H), 5.82 (d, 1H, J=11.4), 6.45 (d, 1H, J=11.4).

Preparation 5

Compound 8

Compound I: Compound 2.

Alkylating agent: 5-Bromo-2-methyl-2-trimethylsilyloxy-pentane (0.6 g).

Method of purification: Chromatography, using 2% to 5% ether in petroleum ether as eluant, followed by crystallisation from methanol.

NMR: δ=0.06 (m, 12H), 0.09 (s, 9H), 0.55 (s, 3H), 0.85 (s, 9H), 0.89 (s, 9H), 0.94 (d, 3H, J=6.6), 1.20 (s, 6H), 1.20–2.10 (m, 18H), 2.31 (bd, 1H), 2.55 (dd, 1H), 2.87 (bd, 1H), 3.15 (dd, 1H), 3.35 (m, 2H), 3.48 (dd, 1H), 4.21 (m, 1H), 4.52 (m, 1H), 4.93 (m, 1H), 4.98 (m, 1H), 5.82 (d, 1H, J=11.4), 6.45 (d, 1H, J=11.4).

Preparation 6

Compound 9

Compound I: Compound 2.

Alkylating agent: Propargyl bromide (0.4 g).

Method of purification: Chromatography, using 2% ether in petroleum ether as eluant, followed by crystallisation from ether-methanol.

NMR: δ=0.05 (m, 12H), 0.55 (s, 3H), 0.86 (d, 9H), 0.89 (s, 9H), 0.95 (d, 3H, J=6.6), 1.20–2.10 (m, 14H), 2.31 (bd, 1H), 2.39 (t, 1H, J=2.3), 2.55 (dd, 1H), 2.87 (bd, 1H), 3.27 (dd, 1H), 3.61 (dd, 1H), 4.11 (d, 2H, J=2.3), 4.21 (m, 1H), 4.53 (m, 1H), 4.93 (m, 1H), 4.97 (m, 1H), 5.82 (d, 1H, J=11.4), 6.45 (d, 1H, J=11.4).

Preparation 7

1(S),3(R)-Bis-[tert-butyl(dimethylsilyl)oxy]-20(R)-(3-hydroxy-3-methyl-1-butoxymethyl-9,10-secopregna-5(E),7(E),10(19)-triene (Compound 7)

NB: This preparation illustrates the protection of the triene system of IV as an SO₂-adduct to allow efficient functional group modification in the side chain.

A solution of compound 6 (100 mg) in a few drops of ether was treated at −10° C. with liquid sulphur dioxide (3 ml). The stirred mixture was allowed to warm spontaneously under a slow stream of nitrogen, and after 30 minutes the residual volatile material was removed on the rotary evaporator. The residue was dissolved in THF (2 ml) and treated with a mixture prepared by adding THF (1 ml) to a solution of mercury II acetate (100 mg) in water (1 ml). The reaction mixture was stirred at 5° C. for 18 hours and then treated with 3N NaOH (3 ml) followed by a solution of NaBH₄ (0.05 g) in 3N NaOH (2 ml). Ethyl acetate was added and the mixture filtered through celite. The organic layer was washed with brine, dried and concentrated in vacuo to give a gum. This was dissolved/suspended in 96% ethanol (4 ml) together with sodium bicarbonate (0.2 g) and the stirred mixture was heated under reflux under nitrogen for 80 minutes. After cooling, the ethyl acetate was added and the mixture was extracted with water. The organic layer was washed with water. The organic layer was washed with brine, dried and concentrated in vacuo to give a residue. Purification by chromatography (silica gel, 5% to 30% ether in petroleum ether as eluent) gave 7.

NMR: δ=0.05 (m, 12H). 0.54 (s, 3H), 0.85 (s, 9H), 0.89 (s, 9H), 0.94 (d, 3H, J=6.6), 1.24 (s, 6H), 1.20–2.10 (m, 16H), 2.30 (bd, 1H) 2.55 (dd, 1H), 2.86 (bd, 1H), 3.32 (dd, 1H), 3.44 (m, 1H), 3.63 (m, 3H), 4.21 (m, 1H), 4.52 (m, 1H), 4.93 (m, 1H), 4.97 (m, 1H), 5.81 (d, 1H, J=11.4), 6.44 (d, 1H, J=11.4).

Preparation 8

Compound 10

A solution of Compound 9 (0.30 g) in dry THF (5 ml), cooled to −70° C. and stirred under N₂, was treated with a solution of butyl-lithium (1.6M in hexanes, 0.35 ml). After stirring for 15 minutes, acetone (0.1 ml) was added. After further 15 minutes the reaction mixture was allowed D to warm to 0° C. and then worked-up (ether). Purification by chromatography (5% to 30% ether in petroleum ether as eluent) gave the title compound.

NMR: γ=0.05 (m, 12H), 0.56 (s, 3H), 0.85 (s, 9H), 0.89 (s, 9H), 0.95 (d, 3H, J=6.6), 1.50 (s, 6H), 1.10–2.10 (m, 15H), 2.30 (bd 1H), 2.54 (dd, 1H), 2.87 (bd, 1H), 3.23 (dd, 1H), 3.62 (dd 1H), 4.13 (s, 2H), 4.20 (m, 1H), 4.52 (m, 1H), 4.93 (m, 1H), 4.97 (m, 1H), 5.82 (d, 1H, J=11.4), 6.44 (d, 1H, J=11.4).

Preparations 9 and 10

Compounds 11 and 12

Using the procedure of Preparation 8, but substituting the appropriate ketone, the following compounds IV were prepared:

from cyclohexanone: Compound 11.

from hexafluoroacetone (added as gas, which was bubbled into the reaction mixture for 1 minute): Compound 12.

General Procedure 2:

Reaction of Compound II with the side chain building block R—YH (Y=S) (Scheme 1) (Preparations 11–13)

Sodium hydride dispersion (55% in oil, 60 mg) was washed with petroleum ether (3×2 ml) under an atmosphere of argon. A solution of R—SH (0.82 mmol) in DMF (dried over molecular sieves) (2 ml) was added, followed by Compound II (ca. 0.5 mmol) in DMF (1 ml). After 30 minutes the reaction mixture was worked up with ether (60 ml). The residue was purified by chromatography (silica gel; ether/petroleum ether 1:3 as eluant) to give IV.

Preparation 11

Compound 13

Compound II: Compound 5( 365 mg ).

R—SH: 2-hydroxy-2-methyl -propane-1-thiol.

NMR: δ=0.06 (m, 12H), 0.55 (s, 3H), 0.86 (s, 9H), 0.89 (s, 9H), 1.01 (d, 3H, J=6.6), 1.26 (s, 6H), 1.15–2.10 (m, 14H), 2.30 (bd, 1H), 2.37 (s, 1H), 2.46 (dd, 1H), 2.55 (dd, 1H), 2.64 (Abq, 2H), 2.85 (m, 2H), 4.21 (m, 1H), 4.52 (m, 1H), 4.94 (m, 1H), 4.98 (m, 1H), 5.82 (d, 1H, J=11.4), 6.44 (d, 1H, J=11.4).

Preparation 12

Compound 14

Compound II: Compound 5 (365 mg ).

R—SH: 3-hydroxy-3-methyl-butane-1-thiol.

NMR: δ=0.05 (m, 12H), 0.55 (s, 3H), 0.85 (s, 9H), 0.89 (s, 9H), 0.99 (d, 3H), 1.22 (s, 6H), 1.25-2.05 (m, 17H), 2.30 (bd, 1H), 2.40 (dd, 1H), 2.58 (m, 3H), 2.83 (m, 2H), 4.21 (m, 1H), 4.52 (m, 1H), 4.93 (m, 1H), 4.98 (m, 1H), 5.81 (d, 1H), 6.44 (d, 1H).

Preparation 13

Compound 15

Compound II: Compound 5 (365 mg).
R—SH: 3-ethyl-3-hydroxy-pentane-1-thiol.

NMR: δ=0.55 (m, 12H), 0.83 (t, 6H), 0.84 (s, 9H), 0.88 (s, 9H), 0.99 (d, 3H), 1.3-2.1 (m, 21H), 1.47 (q, 4H), 2.30 (bd, 1H), 2.40 (dd, 1H), 2.54 (m, 2H), 2.84 (m, 2H), 4.20 (m, 1H), 4.52 (m, 1H), 4.93 (m, 1H), 4.98 (m, 1H), 5.81 (d, 1H), 6.44 (d, 1H).

General Procedure 3

Isomerization of Compounds IV to the corresponding Compounds V

A solution of the compound IV (ca. 0.2 g), anthracene (200 mg) and triethylamine (0.3 ml) in dichloromethane (15 ml) under nitrogen in a Pyrex flask was irradiated with light from a high pressure ultraviolet lamp, type TQ718Z2 (Hanau) at about 10° C. for 30 minutes. The reaction mixture was filtered, concentrated in vacuo and purified by chromatography to give the compound V.

Preparation 14

Compound 16

Starting material: Compound 7.
Chromatography eluant: 5% to 30% ether in petroleum ether.

NMR: δ=0.05 (m, 12H), 0.53 (s, 3H), 0.86 (s, 18H), 0.93 (d, 3H, J=6.7), 1.23 (s, 6H), 1.75 (t, 2H), 1.10-2.05 (m, 14H), 2.20 (dd, 1H), 2.43 (dd, 1H), 2.81 (bd, 1H), 3.31 (dd, 1H), 3.44 (m, 1H), 3.61 (s, 1H), 3.63 (t, 2H), 4.18 (m, 1H), 4.36 (m, 1H), 4.55 (m, 1H), 5.17 (m, 1H), 6.00 (d, 1H, J=11.2), 6.22 (d, 1H, J=11.2).

Preparation 15

Compound 17

Starting material: Compound 8.
Chromatography eluant: 2% to 5% ether in petroleum ether.

NMR: δ=0.05 (m, 12H), 0.09 (s, 9H), 0.54 (s, 3H), 0.87 (s, 18H), 0.93 (d, 3H, J=6.6), 1.20 (s, 6H), 1.10-2.10 (m, 18H), 2.20 (dd, 1H), 2.44 (dd, 1H), 2.81 (bd, 1H), 3.14 (dd, 1H), 3.33 (m, 2H), 3.48 (dd, 1H), 4.18 (m, 1H), 4.36 (m, 1H), 4.85 (m, 1H), 5.17 (m, 1H), 6.01 (d, 1H, J=11.2), 6.22 (d, 1H, J=11.2).

Preparation 16

Compound 18

Starting material: Compound 13.
Chromatography eluant: 25% ether in petroleum ether.

NMR: δ=0.05 (m, 12H), 0.53 (s, 3H), 0.87 (s, 18H), 0.99 (d, 3H, J=6.6), 1.25 (s, 6H), 1.10-2.05 (m, 14H), 2.20 (dd, 1H), 2.40 (s, 1H), 2.45 (m, 2H), 2.63 (ABq, 2H), 2.82 (m, 2H), 4.18 (m, 1H), 4.36 (m, 1H), 4.85 (m, 1H), 5.17 (m, 1H), 6.01 (d, 1H, J=1.2), 6.22 (d, 1H, J=11.2).

Preparation 17

Compound 19

Starting material: Compound 14.
Chromatography eluant: 25% ether in petroleum ether.

NMR: δ=0.05 (m, 12H), 0.54 (s, 3H), 0.86 (s, 18H), 0.98 (d, 3H), 1.23 (s, 6H), 1.2-2.1 (m, 17H), 2.20 (dd, 1H), 2.40 (m, 2H), 2.57 (m, 2H), 2.82 (dd, 2H), 4.18 (m, 1H), 4.35 (m, 1H), 4.85 (d, 1H), 5.17 (bd, 1H), 6.01 (d, 1H), 6.22 (d, 1H).

Preparation 18

Compound 20

Starting material: Compound 15.
Chromatography eluant: 25% ether in petroleum ether.

NMR: δ=0.05 (m, 12H), 0.54 (s, 3H), 0.87 (s, 18H), 0.86 (t, 6H), 0.98 (d, 3H), 1.1-2.05 (m, 17H), 1.47 (q, 4H), 2.20 (dd, 1H), 2.40 (m, 2H), 2.52 (dd, 2H), 2.81 (dd, 1H), 4.17 (m, 1H), 4.36 (m, 1H), 4.84 (d, 1H), 5.16 (d, 1H), 6.00 (d, 1H), 6.21 (d, 1H).

Preparation 19

Compound 21

Starting material: Compound 10.
Chromatography eluant: 25% ether in petroleum ether.

NMR: δ=0.05 (m, 6H), 0.55 (s, 3H), 0.86 (s, 18H), 0.94 (d, 3H), 1.20-2.1 (m, 21H), 1.49 (s, 6H), 2.20 (dd, 1H), 2.44 (dd, 1H), 2.81 (dd, 1H), 3.22 (t, 1H), 3.62 (dd, 1H), 4.13 (s, 2H), 4.17 (m, 1H), 4.36 (m, 1H), 4.85 (d, 1H), 5.17 (m, 1H), 6.01 (d, 1H), 6.21 (d, 1H).

Preparation 20

Compound 22

Compound I: Compound 2.
Alkylating agent: 1-Bromo-3-ethyl-pent-2-ene (0.3 g).
Method of purification: Chromatography, using 2% ether in petroleum ether as eluant.

NMR: δ=0.05 (m, 12H), 0.55 (s, 3H), 0.86 (s, 9H), 0.89 (s, 9H), 0.95 (d, 3H, J=6.6), 0.97 (t, 3H), 1.02 (t, 3H), 1.20-2.10 (m, 14H), 2.07 (m, 4H), 2.31 (bd, 1H), 2.55 (dd, 1H), 2.87 (bd, 1H), 3.15 (dd, 1H), 3.52 (dd, 1H), 3.95 (m, 2H), 4.21 (m, 1H), 4.53 (m, 1H), 4.93 (m, 1H), 4.98 (m, 1H), 5.28 (m, 1H), 5.82 (d, 1H, J=11.4), 6.45 (d, 1H, J=11.4).

Preparation 21

Compound 23

Compound I: Compound 2.
Alkylating agent: 5-Bromo-2-methyl -2-trimethylsilyloxy-pent- 3(E)-ene(0.4 g).
Method of purification: Chromatography, using 2% ether in petroleum ether as eluant, followed by crystallisation from ether-methanol.

NMR: δ=0.06 (m, 12H), 0.09 (s, 9H), 0.55 (s, 3H), 0.85 (s, 9H), 0.89 (s, 9H), 0.95 (d, 3H, J=6.6), 1.31 (s, 6H), 1.20-2.10 (m, 16H), 2.31 (bd, 1H), 2.55 (dd, 1H), 2.87 (bd, 1H), 3.15 (dd, 1H), 3.51 (dd, 1H), 3.92 (d, 2H), 4.21 (m, 1H), 4.52 (m, 1H), 4.93 (m, 1H), 4.98 (m, 1H), 5.63 (dt, 1H), 5.77 (d, 1H), 5.82 (d, 1H, J=11.4), 6.45 (d, 1H, J=11.4).

General Procedure 6

Reaction of Compound II with the side chain building block R—YH (Y=O) (Scheme 1)

Sodium hydride dispersion (55% in oil, 1 mmol) was added to a solution of R—OH (1 mmol) in DMF (5 ml). After stirring for 15 minutes Compound II (0.5 mmol) was added. The reaction mixture was stirred overnight and worked up with water and ethyl acetate. The residue was purified by chromtography (silica gel; ether/petroleum ether 1:3 as eluant) to give IV.

The side chain building blocks R—OH used in Preparations 23-28 were prepared as follows:

A solution of the appropriate methyl hydroxybenzoate (50 mmol) in dry THF (60 ml) was added with stirring to a boiling solution of Grignard reagent ($CH_3MgI$ or $C_2H_5MgBr$, freshly prepared from magnesium (300 mmol)) in dry ether (90 ml). The mixture was refluxed for 15 minutes, cooled, hydrolyzed with water and neutralized with hydrochloric acid. The product was extracted with ethyl acetate and purified by crystallization.

Preparation 22

Compound 24

Method: General Procedure 1.
Compound I: Compound 2.
Alkylating agent: 6-bromo-2-methyl-2-trimethylsilyloxy-hexane (1.0 g).
Method of purification: Chromatography using 2% ether in petroleum ether as eluant.

NMR: $\delta$=0.05 (m, 12H), 0.09 (s, 9H), 0.55 (s, 3H), 0.86 (s, 9H), 0.89 (s, 9H), 0.94 (d, 3H), 1.19 (s, 6H), 1.05-2.10 (m, 20H), 2.30 (bd, 1H), 2.55 (dd, 1H), 2.87 (bd, 1H), 3.15 (t, 1H), 3.37 (m, 2H), 3.47 (dd, 1H), 4.21 (m, 1H), 4.52 (m, 1H), 4.93 (m, 1H), 4.98 (m, 1H), 5.82 (d, 1H), 6.45 (d, 1H).

Preparation 23

Compound 25

Method: General Procedure 6.
Compound II: Compound 5.
R—OH: 2-(2-hydroxy-2-propyl)-phenol, m.p.: 42°-43° C. (from petroleum ether).

NMR: $\delta$=0.05 (s, 12H), 0.60 (s, 3H), 0.86 (s, 9H), 0.89 (s, 9H), 1.13 (d, 3H), 1.63 (s, 3H), 1.64 (s, 3H), 1.25-2.10 (m, 15H), 2.31 (bd, 1H), 2.55 (dd, 1H), 2.85 (bd, 1H), 4.03 (d, 2H), 4.22 (m, 1H), 4.46 (s, 1H), 4.51 (dd, 1H), 4.93 (bs, 1H), 4.97 (bs, 1H), 5.83 (d, 1H), 6.43 (d, 1H), 6.91 (m, 2H), 7.20 (m, 1H), 7.31 (m, 1H).

Preparation 24

Compound 26

Method: General Procedure 6.
Compound II: Compound 5.
R—OH: 2-(3-hydroxy-3-pentyl)-phenol, m.p.: 55°-56° C. (from petroleum ether).

NMR: $\delta$=0.06 (m, 12H), 0.59 (s, 3H), 0.80 (bt, 6H), 0.86 (s, 9H), 0.89 (s, 9H), 1.11 (d, 3H), 1.15-2.15 (m, 18H), 2.31 (bd, 1H), 2.55 (dd, 1H), 2.86 (bd, 1H), 3.98 (m, 2H), 4.08 (s, 1H), 4.22 (m, 1H), 4.52 (m, 1H), 4.93 (m, 1H), 4.98 (m, 1H), 5.83 (d, 1H), 6.44 (d, 1H), 6.86 (d, 1H), 6.93 (dt, 1H), 7.19 (dt, 1H), 7.25 (dd, 1H).

Preparation 25

Compound 27

Method: General Procedure 6.
Compound II: Compound 5.
R—OH: 3-(2-hydroxy-2-propyl)-phenol, m.p.: 103°-104° C. (from toluene).

NMR: $\delta$=0.06 (m, 12H), 0.59 (s, 3H), 0.86 (s, 9H), 0.89 (s, 9H), 1.06 (d, 3H), 1.57 (s, 6H), 1.20-2.15 (m, 15H), 2.32 (bd, 1H), 2.57 (dd, 1H), 2.86 (bd, 1H), 3.77 (dd, 1H), 4.01 (dd, 1H), 4.22 (m, 1H), 4.52 (m, 1H), 4.93 (m, 1H), 4.98 (m, 1H), 5.84 (d, 1H), 6.45 (d, 1H), 6.75 (m, 1H), 7.02 (m, 1H), 7.05 (m, 1H), 7.24 (t, 1H).

Preparation 26

Compound 28

Method: General Procedure 6.
Compound II: Compound 5.
R—OH: 3-(3-hydroxy-3-pentyl)-phenol, m.p.: 78°-79° C. (from toluene).

NMR: $\delta$=0.06 (m, 12H), 0.59 (s, 3H), 0.76 (t, 6H), 0.86 (s, 9H), 0.90 (s, 9H), 1.06 (d, 3H), 1.20-2.03 (m, 18H), 2.06 (bt, 1H), 2.32 (bd, 1H), 2.55 (dd, 1H), 2.86 (bd, 1H), 3.75 (m, 1H), 4.01 (dd, 1H), 4.22 (m, 1H), 4.52 (m, 1H), 4.93 (m, 1H), 4.98 (m, 1H), 5.83 (d, 1H), 6.44 (d, 1H), 6.72 (m, 1H), 6.89 (bd, 1H), 6.94 (m, 1H), 7.22 (t, 1H).

Preparation 27

Compound 29

Method: General Procedure 6.
Compound II: Compound 5.
R—OH: 4-(2-hydroxy-2-propyl)-phenol, m.p.: 98.5°-103° C. (from ethyl acetate).

NMR: $\delta$=0.06 (m, 12H), 0.59 (s, 3H), 0.89 (s, 9H), 0.86 (s, 9H), 1.05 (d, 3H), 1.56 (s, 6H), 1.15-2.10 (m, 15H), 2.31 (bd, 1H), 2.55 (dd, 1H), 2.86 (bd, 1H), 3.75 (dd, 1H), 3.99 (dd, 1H), 4.22 (m, 1H), 4.52 (m, 1H), 4.93 (m, 1H), 4.98 (m, 1H), 5.83 (d, 1H), 6.44 (d, 1H), 6.84 (m, 2H), 7.38 (m, 2H).

Preparation 28

Compound 30

Method: General Procedure 6.
Compound II: Compound 5.
R—OH: 4-(3-hydroxy-3-pentyl)-phenol, m.p.: 140°-142° C. (from toluene).

NMR: $\delta$=0.06 (m, 12H), 0.59 (s, 3H), 0.75 (t, 6H), 0.89 (s, 9H), 0.86 (s, 9H), 1.06 (d, 3H), 1.25-2.00 (m, 18H), 2.07 (t, 1H), 2.31 (bd, 1H), 2.55 (dd, 1H), 2.86 (bd, 1H), 3.73 (dd, 1H), 4.00 (dd, 1H), 4.22 (m, 1H), 4.52 (dd, 1H), 4.93 (m, 1H), 4.98 (m, 1H), 5.83 (d, 1H), 6.44 (d, 1H), 6.84 (m, 2H), 7.27 (m 2H).

Preparation 29

Compound 31

Method: General Procedure 6.
Compound II: Compound 5.
R—OH: 3-(hydroxymethyl)-phenol.

NMR: $\delta$=0.06 (m, 12H), 0.59 (s, 3H), 0.85 (s, 9H), 0.89 (s, 9H), 1.06 (d, 3H), 1.15-2.15 (m, 15H), 2.31 (bd, 1H), 2.55 (dd, 1H), 2.86 (bd, 1H), 3.78 (dd, 1H), 3.99 (dd, 1H), 4.22 (m, 1H), 4.52 (m, 1H), 4.66 (d, 2H), 4.93 (m, 1H), 4.97 (m, 1H), 5.83 (d, 1H), 6.44 (d, 1H), 6.80 (m, 1H), 6.90 (bs, 1H), 6.91 (m, 1H), 7.25 (t, 1H).

Preparation 30

Compound 32

Method: General Procedure 3.
Starting material: Compound 24.
Chromatography eluant: 2% ether in petroleum ether.
NMR: δ=0.05 (m, 12H), 0.09, (s, 9H), 0.54 (s, 3H), 0.87 (s, 18H), 0.93 (d, 3H), 1.19 (s, 6H), 1.2–2.0 (m, 20H), 2.21 (dd, 1H), 2.44 (dd, 1H), 2.81 (dd, 1H), 3.14 (dd, 1H), 3.38 (m, 2H), 3.48 (dd, 1H), 4.16 (m, 1H), 4.36 (m, 1H), 4.85 (d, 1H), 5.17 (m, 1H), 6.00 (d, 1H), 6.22 (d, 1H).

Preparation 31

Compound 33

Method: General Procedure 3.
Starting material: Compound 25.
Chromatography eluant: 5 to 20% ether in hexane.
NMR: δ=0.06 (m, 12H), 0.59 (s, 3H), 0.86 (s, 9H), 0.87 (s, 9H), 1.12 (d, 3H), 1.63 (s, 3H), 1.64 (s, 3H), 1.15–2.10 (m, 14H), 2.20 (dd, 1H), 2.43 (dd, 1H), 2.80 (bd, 1H), 4.02 (m, 2H), 4.17 (m, 1H), 4.37 (m, 1H), 4.46 (s, 1H), 4.86 (m, 1H), 5.18 (m, 1H), 6.02 (d, 1H), 6.21 (d, 1H), 6.88 (bd, 1H), 6.93 (dt, 1H), 7.21 (dt, 1H), 7.31 (dd, 1H).

Preparation 32

Compound 34

Method: General Procedure 3.
Starting material: Compound 26.
Chromatography eluant: 1 to 15% ether in hexane.
NMR: δ=0.05 (m, 12H), 0.58 (s, 3H), 0.79 (t, 6H), 0.86 (s, 9H), 0.87 (s, 9H), 1.10 (d, 3H), 1.17–2.12 ( m, 18H), 2.21 (dd, 1H), 2.43 (dd, 1H), 2.80 (bd, 1H), 3.97 (m, 2H), 4.08 (s, 1H), 4.18 (m, 1H), 4.37 (m, 1H), 4.86 (m, 1H), 5.18 (m, 1H), 6.02 (d, 1H), 6.21 (d, 1H), 6.86 (d, 1H), 6.93 (dt, 1H), 7.19 (dt, 1H), 7.25 (dd, 1H).

Preparation 33

Compound 35

Method: General Procedure 3.
Starting material: Compound 27.
Chromatography eluant: 10–35% ether in hexane.
NMR: δ=0.06 (m, 12H), 0.58 (s, 3H), 0.86 (s, 9H), 0.87 (s, 9H), 1.05 (d, 3H), 1.57 (s, 6H), 1.17–2.12 (m, 15H), 2.21 (dd, 1H), 2.44 (dd, 1H), 2.81 (bd, 1H), 3.76 (m, 1H), 4.01 (dd, 1H), 4.18 (m, 1H), 4.37 (m, 1H), 4.86 (m, 1H), 5.18 (m, 1H), 6.02 (d, 1H), 6.22 (d, 1H), 6.75 (m, 1H), 7.02 (m, 1H), 7.05 (m, 1H), 7.24 (t, 1H).

Preparation 34

Compound 36

Method: General Procedure 3.
Starting material: Compound 28.
Chromatography eluant: 10–35% ether in hexane.
NMR: δ=0.06 (m, 12H), 0.58 (s, 3H), 0.76 (t, 6H), 0.86 (s, 9H), 0.87 (s, 9H), 1.06 (d, 3H), 1.15–2.15 (m, 19H), 2.21 (dd, 1H), 2.44 (dd, 1H), 2.81 (bd, 1H), 3.74 (m, 1H), 4.01 (dd, 1H), 4.18 (m, 1H), 4.37 (m, 1H), 4.86 (m, 1H), 5.18 (m, 1H), 6.02 (d, 1H), 6.22 (d, 1H), 6.72 (m, 1H), 6.89 (bd, 1H), 6.94 (m, 1H), 7.22 (t, 1H).

Preparation 35

Compound 37

Method: General Procedure 3.
Starting material: Compound 29.
Chromatography eluant: 10–35% ether in hexane.
NMR: δ=0.05 (m, 12H), 0.57 (s, 3H), 0.87 (s, 9H), 0.86 (s, 9H), 1.04 (d, 3H), 1.56 (s, 6H), 1.20–2.05 (m, 15H), 2.20 (dd, 1H), 2.43 (dd, 1H), 2.81 (bd, 1H), 3.73 (dd, 1H), 3.99 (dd, 1H), 4.18 (m, 1H), 4.37 (m, 1H), 4.86 (d, 1H), 5.18 (m, 1H), 6.02 (d, 1H), 6.22 (d, 1H), 6.84 (m, 2H), 7.39 (m, 2H).

Preparation 36

Compound 38

Method: General Procedure 3.
Starting material: Compound 31.
Chromatography eluant: 10–35% ether in hexane.
NMR: δ=0.05 (m, 12H), 0.58 (s, 3H), 0.75 (t, 6H), 0.88 (s, 9H), 0.87 (s, 9H), 1.05 (d, 3H), 1.20–2.10 (m, 19H), 2.20 (dd, 1H), 2.43 (dd, 1H), 2.81 (bd, 1H), 3.72 (dd, 1H), 4.00 (dd, 1H), 4.17 (m, 1H), 4.38 (m, 1H), 4.86 (bd, 1H), 5.18 (m, 1H), 6.02 (d, 1H), 6.22 (d, 1H), 6.84 (m, 2H), 7.26 (m, 2H).

Preparation 37

Compound 39

Method: General Procedure 3.
Starting material: Compound 31.
Chromatography eluant: 1–30% ether in hexane.
NMR: δ=0.06 (m, 12H), 0.58 (s, 3H), 0.86 (s, 9H), 0.87 (s, 9H), 1.05 (d, 3H), 1.15–2.10 (m, 15H), 2.21 (dd, 1H), 2.44 (dd, 1H), 2.81 (bd, 1H), 3.76 (dd, 1H), 3.99 (dd, 1H), 4.18 (m, 1H), 4.37 (m, 1H), 3.66 (d, 2H), 4.86 (m, 1H), 5.18 (m, 1H), 6.02 (d, 1H), 6.22 (d, 1H), 6.80 (m, 1H), 6.90 (bs, 1H), 6.91 (m, 1H), 7.25 (t, 1H).

Preparation 38

Compound 40

Method: General Procedure 3.
Compound IV: Compound 23.
Chromatography eluant: 2% ether in petroleum ether.
NMR: δ=0.06 (m, 12H), 0.10 (s, 9H), 0.53 (s, 3H), 0.87 (s, 18H), 0.94 (d, 3H), 1.31 (bs, 6H), 1.15–2.10 (m, 14H), 2.22 (dd, 1H), 2.44 (dd, 1H), 2.81 (dd, 1H), 3.14 (m, 1H), 3.51 (dd, 1H), 3.92 (m, 2H), 4.18 (m, 1H), 4.36 (m, 1H), 4.86 (m, 1H), 5.17 (m, 1H), 5.63 (dt, 1H), 5.78 (d, 1H), 6.01 (d, 1H), 6.22 (d, 1H).

Preparation 39

Compound 41

The compound was prepared using the method of Preparation 7, except using compound 22 as starting material instead of compound 6.
NMR: δ=0.05 (m, 12H), 0.54 (s, 3H), 0.85 (s, 9H), 0.86 (t, 6H), 0.89 (s, 9H), 0.94 (d, 3H), 1.20–2.10 (m, 20H), 2.30 (bd, 1H), 2.55 (dd, 1H), 2.86 (bd, 1H), 3.30 (m, 1H), 3.38 (s, 1H), 3.43 (dd, 1H), 3.59 (t, 2H), 4.21 (m, 1H), 4.52 (m, 1H), 4.93 (m, 1H), 4.98 (m, 1H), 5.81 (d, 1H), 6.44 (d, 1H).

Preparation 40

Compound 42

Method: General Procedure 3.

Compound IV: Compound 41.

Chromatography eluant: 30% ether in petroleum ether.

This compound was used as starting material in Example 16.

Preparation 41

Oxidation of Compound 15 to the corresponding isomeric sulphoxides (Compounds 43 and 44)

To a mixture of compound 15 (73 mg), sodium hydrogen carbornate (10 mg), a 2% (w/v) solution of sodium tungstate, dihydrate (10 $\mu$l) and methanol (0.5 ml) was added 30% hydrogen peroxide (24 $\mu$l) and chloroform (0.5 ml). The mixture was stirred at 22° C. for 3 hours. Water (10 ml) was added and the mixture worked up (methylene chloride) to give a residue which was chromatographed (9 g silica gel; ethyl acetate as eluant) to give Compound 43, Rf 0.4, NMR: $\delta=0.05$ (m, 12H), 0.61 (s, 3H), 0.84 (s, 9H), 0.88 (t, 6H), 0.89 (s, 9H), 1.11 (d, 3H), 1.5-2.22 (m, 21H), 2.28 (t, 1H), 2.29 (bd, 1H), 2.56 (dd, 1H), 2.75 (t, 2H), 2.88 (dd, 1H), 3.11 (dd, 1H), 4.21 (m, 1H), 4.53 (m, 1H), 4.94 (m, 1H), 4.97 (m, 1H), 5.82 (d, 1H), 6.43 (d, 1H); and Compound 44, Rf 0.3, NMR: $\delta=0.05$ (m, 12H), 0.57 (s, 3H), 0.85 (s, 9H), 0.89 (s, 9H), 0.87 (t, 6H), 1.08 (d, 3H), 1.00-2.20 (m, 21H), 2.30 (bd, 1H), 2.54 (dd, 1H), 2.68 (m, 2H), 2.86 (m, 2H), 2.99 (dd, 1H), 4.21 (m, 1H), 4.52 (m, 1H), 4.93 (m, 1H), 4.97 (m, 1H), 5.82 (d, 1H), 6.43 (d, 1H).

Preparation 42

Oxidation of Compounds 43 and/or the corresponding sulphone (Compound 45)

Compound 43 or Compound 44 or a mixture of Compound 43 and Compound 44 (24 mg) was stirred with methanol (0.2 ml), sodium hydrogen carbonate (10 mg), 2% (w/v) sodium tungstate, dihydrate (10 $\mu$l), and 30% hydrogen peroxide (12 $\mu$l) at 50° C. for 2 hours. Water (15 ml) was added, and the mixture was worked up (methylene chloride) to give a residue which was chromatographed (5 g silica gel, ethyl acetate as eluant) to give Compound 45, Rf 0.75, NMR: $\delta=0.05$ (m, 12H), 0.59 (s, 3H), 0.85 (s, 9H), 0.87 (t, 6H), 0.89 (s, 9H), 1.18 (d, 3H), 1.10-2.10 (m, 21H), 2.28 (bd, 2.55 (dd, 1H), 2.74 (dd, 1H), 2.87 (dd, 1H), 3.05 (m, 2H), 3.32 (dd, 1H), 4.20 (m, 1H), 4.52 (m, 1H), 4.93 (m, 1H), 4.97 (m, 1H), 5.82 (d, 1H), 6.42 (d, 1H).

Preparation 43

Compound 46

Method: General Procedure 2.
Compound II: Compound 5 (365 mg).
R—SH: methyl 4-mercaptobutyrate.
Purification by chromatography (silica gel, ether/petroleum ether 1:5 as eluant)
NMR: $\delta=0.06$ (m, 12H), 0.54 (s, 3H), 0.85 (s, 9H), 0.89 (s, 9H), 0.99 (d, 3H), 1.15-2.15 (m, 16H), 2.31 (bd, 1H), 2.36 (dd, 1H), 2.44 (t, 2H), 2.52 (t, 2H), 2.55 (dd, 1H), 2.76 (dd, 1H), 2.87 (dd, 1H), 3.66 (s, 3H), 4.21 (m, 1H), 4.52 (m, 1H), 4.93 (m, 1H), 4.98 (m, 1H), 5.81 (d, 1H), 6.44 (d, 1H).

Preparation 44

Reaction of Compound II with 3-mercaptobenzoic acid (Compound 47)

Sodium hydride dispersion (55% in oil, 514 mg) was washed with petroleum ether (3×5 ml) under an atmosphere of argon. DMF (dried over molecular sieves) (5 ml) and 3-mercaptobenzoic acid (462 mg) was added, followed by Compound II (2 mmol) in DMF (3 ml). After 40 minutes, the reaction mixture was heated for 10 minutes at 100° C. After cooling to room temperature, water (60 ml) was carefully added, followed by hydrochloric acid (1M) to pH 5. Work-up with ether and purification by chromatography (15 g silica gel, ether as eluant) gave Compound 47.

NMR: $\delta=0.05$ (m, 12H), 0.53 (s, 3H), 0.85 (s, 9H), 0.89 (s, 9H), 1.04 (d, 3H), 1.15-1.98 (m, 13H), 2.05 (bt, 1H), 2.31 (bd, 1H), 2.53 (dd, 1H), 2.83 (m, 2H), 3.25 (dd, 1H), 4.21 (m, 1H), 4.52 (m, 1H), 4.93 (m, 1H), 4.98 (m, 5.82 (m, 1H), 6.44 (d, 1H), 7.33 (bt, 1H), 7.51 (bd, 1H), 7.84 (bd, 1H), 8.01 (bs, 1H).

Preparation 45

Compound 48

Compound 47 (590 mg) was dissolved in ether (50 ml), and an etheral solution of diazomethane was added until a yellow colour persisted. The reaction mixture was concentrated in vacuo, and the residue chromatographed (25 g silica gel, ether/petroleum ether 3:1 as eluant) to give give Compound 48.

NMR: $\delta=0.05$ (m, 12H), 0.54 (s, 3H), 0.85 (s, 9H), 0.89 (s, 9H), 1.04 (d, 3H), 1.15-2.00 (m, 13H), 2.05 (bt, 1H), 2.31 (bd, 1H), 2.54 (dd, 1H), 2.78 (dd, 1H), 2.87 (dd, 1H), 3.28 (dd, 1H), 3.90 (s, 3H), 4.21 (m, 1H), 4.53 (m, 1H), 4.93 (m, 1H), 4.97 (m, 1H), 5.82 (d, 1H), 6.44 (d, 1H), 7.32 (bt, 1H), 7.48 (m, 1H), 7.80 (m, 1H), 7.97 (t, 1H).

Preparation 46

Compound 49

Following the procedure described in Preparation 8, but replacing acetone with 3-pentanone, gave the title compound.

NMR: $\delta=0.05$ (s, 12H), 0.55 (s, 3H), 0.85 (s, 9H), 0.89 (s, 9H), 0.94 (d, 3H), 1.02 (t, 6H), 1.20-2.10 (m, 19H), 2.29 (d, 1H), 2.52 (dd, 1H), 2.86 (bd, 1H), 3.22 (t, 1H), 3.64 (dd, 1H), 4.16 (ABq, 2H), 4.21 (m, 1H), 4.51 (dd 1H), 4.93 (bs, 1H), 4.97 (bs, 1H), 5.81 (d, 1H), 6.44 (d, 1H).

Preparation 47

Compound 50

Method: General Procedure 3.
Starting material: Compound 43.
Chromatography eluant: ethyl acetate.
NMR: $\delta=0.05$ (m, 12H), 0.59 (s, 3H), 0.85 (s, 9H), 0.86 (s, 9H), 0.87 (t, 6H), 1.09 (d, 3H), 1.00-2.35 (m, 23H), 2.43 (dd, 1H), 2.74 (t, 2H), 2.82 (bd, 1H), 3.10 (dd, 1H), 4.18 (m, 1H), 4.35 (m, 1H), 4.84 (m, 1H), 5.16 (m, 1H), 6.01 (d, 1H), 6.21 (d, 1H).

Preparation 48

Compound 51

Method: General Procedure 3.
Starting material: Compound 44.
Chromatography eluant: ethyl acetate.
NMR: $\delta=0.04$ (m, 12H), 0.54 (s, 3H), 0.86 (s, 18H), 0.87 (t, 6H), 1.06 (d, 3H), 1.15-2.50 (m, 23H), 2.67 (m, 2H), 2.84 (m, 2H), 3.00 (dd, 1H), 4.17 (m, 1H), 4.35 (m, 1H), 4.84 (m, 1H), 5.16 (m, 1H), 6.00 (d, 1H), 6.20 (d, 1H).

Preparation 49

Compound 52

Method: General Procedure 3.
Starting material: Compound 45.
Chromatography eluant: 25% ethyl acetate in petroleum ether.

NMR: δ=0.05 (m, 12H), 0.58 (s, 3H), 0.86 (s, 18H), 0.87 (t, 6H), 1.17 (d, 3H), 1.05–2.10 (m, 20H), 2.20 (m, 2H), 2.44 (dd, 1H), 2.73 (dd, 1H), 2.83 (bd, 1H), 3.05 (dd, 2H), 3.32 (dd, 1H), 4.18 (m, 1H), 4.36 (m, 1H), 4.83 (m, 1H), 5.17 (m, 1H), 6.01 (d, 1H), 6.21 (d, 1H).

Preparation 50

Compound 53

Method: General Procedure 3.
Starting material: Compound 46.
Chromatography eluant: 12.5% ether in petroleum ether.

NMR: δ=0.05 (m, 12H), 0.54 (s, 3H), 0.87 (s, 18H), 0.98 (d, 3H), 1.15–2.10 (m, 16H), 2.22 (dd, 2H), 2.36 (dd, 1H), 2.43 (m, 1H), 2.44 (t, 2H), 2.52 (t, 2H), 2.76 (dd, 1H), 2.82 (bd, 1H), 3.66 (s, 3H), 4.18 (m, 1H), 4.36 (m, 1H), 4.85 (m, 1H), 5.17 (m, 1H), 6.00 (d, 1H), 6.22 (d, 1H).

Preparation 51

Compound 54

Method: General Procedure 3.
Starting material: Compound 48.
Chromatography eluant: 5% ether in petroleum ether.

NMR: δ=0.05 (m, 12H), 0.52 (s, 3H), 0.86 (s, 18H), 1.03 (d, 3H), 1.15–2.07 (m, 14H), 2.20 (dd, 2H), 2.43 (dd, 1H), 2.77 (dd, 1H), 2.82 (bd, 1H), 3.28 (dd, 1H), 3.90 (s, 3H), 4.17 (m, 1H), 4.36 (m, 1H), 4.85 (m, 1H), 5.17 (m, 1H), 6.00 (d, 1H), 6.22 (d, 1H), 7.32 (t, 1H), 7.48 (m, 1H), 7.79 (m, 1H), 7.97 (m, 1H).

Preparation 52

Compound 55

Method: General Procedure 3.
Starting material: Compound 49.
Chromatography eluant: 25% ether in petroleum ether.

NMR: δ=0.05 (s, 12H), 0.54 (s, 3H), 0.81 (s, 18H), 0.94 (d, 3H), 1.03 (t, 6H), 1.20–2.0 (m, 19H), 2.20 (dd, 1H), 2.44 (dd, 1H), 2.81 (bd, 1H), 3.22 (t, 1H), 3.64 (dd, 1H), 4.16 (ABq, 2H), 4.18 (m, 1H), 4.36 (m, 1H), 4.85 (bs, 1H), 5.17 (bs, 1H), 6.00 (d, 1H), 6.22 (d, 1H).

General Procedure 7

Reaction of side chain carboxylic esters with methyl lithium (Preparations 53–54)

To a solution of Compound V (0.13 mmol) in dry THF (1.5 ml) under argon atmosphere at 0° C. was added a solution of methyl lithium in ether (1.6M, 0.24 ml). After stirring for 30 minutes, water (15 ml) was added, and the reaction mixture was worked up with ether. Purification by chromatography (10 g silica gel, 25% ether in petroleum ether) gave the tertiary alcohols V.

Preparation 53

Compound 56

Method: General Procedure 7.
Starting material: Compound 53.

NMR: δ=0.05 (m, 12H), 0.53 (s, 3H), 0.87 (s, 18H), 0.98 (d, 3H), 1.20 (s, 6H), 1.07–2.07 (m, 19H), 2.20 (dd, 2H), 2.34 (dd, 1H), 2.44 (dd, 1H), 2.50 (t, 2H), 2.77 (m, 2H), 4.18 (m, 1H), 4.36 (m, 1H), 4.85 (m, 1H), 5.17 (m, 1H), 6.00 (d, 1H), 6.22 (d, 1H).

Preparation 54

Compound 57

Method: General Procedure 7.
Starting material: Compound 54.

NMR: δ=0.07 (m, 12H), 0.52 (s, 3H), 0.89 (s, 18H), 1.05 (d, 3H), 1.57 (s, 6H), 1.18–2.12 (m, 15H), 2.23 (dd, 1H), 2.46 (dd, 1H), 2.74 (dd, 1H), 2.83 (dd, 1H), 3.28 (dd, 1H), 3.28 (dd, 3H), 4.20 (m, 1H), 4.38 (m, 1H), 4.87 (m, 1H), 5.19 (m, 1H), 6.02 (d, 1H), 6.24 (d, 1H), 7.25 (m, 3H), 7.50 (m, 1H).

Preparation 55

Compound 58

To a solution of Compound 54 (100 mg) in toluene (0.4 ml) was added a solution of sodium bis(2-methoxyethoxy)aluminium hydride in toluene (3.4M, 41 μl), and the mixture was heated to 50° C. for 15 minutes. After cooling to room temperature, water (10 ml) was added, and the mixture was worked up with ethyl acetate. Purification by chromatography (12 g silica gel, 20% ether in petroleum ether as eluant) gave Compound 58.

NMR: δ=0.05 (m, 12H), 0.51 (s, 3H), 0.86 (s, 18H), 1.03 (d, 3H), 1.18–2.10 (m, 15H), 2.20 (dd, 1H), 2.43 (dd, 1H), 2.75 (dd, 1H), 2.82 (bd, 1H), 3.25 (dd, 1H), 4.18 (m, 1H), 4.37 (m, 1H), 4.65 (d, 2H), 4.85 (m, 1H), 5.17 (m, 1H), 6.00 (d, 1H), 6.22 (d, 1H), 7.13 (m, 1H), 7.24 (m, 2H), 7.32 (s, 1H).

Preparation 56

Compound 59

Sodium hydride dispersion (55% in oil, 7.5 mmol) was added with stirring to a solution of catechol (7.5 mmol) in DMF (50 ml). After stirring for 15 minutes, compound 5 (0.75 mmol) was added. The mixture was stirred overnight and worked up with water and ethyl acetate. The residue was purified by chromatography (silica gel; ether/hexane 1:9).

NMR: δ=0.06 (s, 12H), 0.60 (s, 3H), 0.86 (s, 9H), 0.89 (s, 9H), 1.09 (d, 3H), 1.25–2.15 (m, 14H), 2.31 (bd, 1H), 2.55 (dd, 1H), 2.88 (bd, 1H), 3.87 (dd, 1H), 4.07 (dd, 1H), 4.21 (m, 1H), 4.52 (m, 1H), 4.94 (m, 1H), 4.98 (m, 1H), 5.61 (s, 1H), 5.84 (d, 1H), 6.44 (d, 1H), 6.75–7.0 m, 4H).

Preparation 57

Compound 60

This compound was prepared as described in Preparation 56 substituting resorcinol for catechol. Purification by chromatography (silica gel; ether/hexane 3:7).

NMR: δ=0.05 (m, 12H), 0.58 (s, 3H), 0.86 (s, 9H), 0.89 (s, 9H), 1.05 (d, 3H), 1.20–2.10 (m, 14H), 2.31 (bd, 1H), 2.55 (dd, 1H), 2.86 (m, 1H), 3.71 (m, 1H), 3.96 (dd, 1H), 4.22 (m, 1H), 4.52 (m, 1H), 4.76 (s, 1H), 4.93 (m, 1H), 4.97 (m, 1H), 5.84 (d, 1H), 6.42 (m, 4H), 7.10 (m, 1H).

Preparation 58

Compound 61

Method: General Procedure 3.
Starting material: Compound 59.
Chromatography eluant: ether/hexane 1:9.
NMR: δ=0.05 (m, 12H), 0.58 (s, 3H), 0.86 (s, 9H), 0.87 (s, 9H), 1.07 (d, 3H), 1.25–2.05 (m, 14H), 2.21 (dd, 1H), 2.44 (dd, 1H), 2.82 (bd, 1H), 3.86 (dd, 1H), 4.07 (dd, 1H), 4.18 (m, 1H), 4.37 (m, 1H), 4.86 (m, 1H), 5.18 (m, 1H), 5.61 (s, 1H), 6.02 (d, 1H), 6.22 (d, 1H), 6.75–7.00 (m, 4H).

Preparation 59

Compound 62

Method: General Procedure 3.
Starting material: Compound 60.
Chromatography eluant: ether/hexane 3:7.
NMR: δ=0.05 (m, 12H), 0.57 (s, 3H), 0.88 (s, 18H), 1.04 (d, 3H), 1.20–2.05 (m, 14H), 2.21 (dd, 1H), 2.44 (dd, 1H), 2.81 (bd, 1H), 3.70 (dd, 1H), 3.96 (dd, 1H), 4.18 (m, 1H), 4.36 (m, 1H), 4.76 (s, 1H), 4.86 (m, 1H), 5.18 (m, 1H), 6.02 (d, 1H), 6.22 (d, 1H), 6.40 (m, 2H), 6.46 (m, 1H), 7.10 (m, 1H).

Preparation 60

Compound 63

Thioacetic acid (57 mg) and cesium carbonate (90 mg) was stirred with methanol (2 ml) for 15 minutes and evaporated to dryness in vacuo. A solution of Compound 5 (366 mg) in dry DMF (2.5 ml) was added, and the mixture was stirred for 5 hours. Work-up with ether and chromatography with ether/p-ether 2:98 as eluant gave 1 (S),3(R)-bis(tert-butyldimethylsilyloxy)-20(R)-(acetylthiomethyl)-9,10-seco-pregna-5(E),7(E),10(19)-triene; NMR: δ=0.05 (m, 12H), 0.60 (s, 3H), 0.85 (s, 9H), 0.89 (s, 9H), 0.90 (d, 3H), 1.20–2.10 (m, 14H), 2.27 (d, 1H), 2.31 (s, 3H), 2.55 (m, 1H), 2.58 (dd, 1H), 2.86 (m, 1H), 3.38 (dd, 1H), 4.21 (m, 1H), 4.52 (m, 1H), 4.93 (m, 1H), 4.98 (m, 1H), 5.82 (d, 1H), 6.44 (d, 1H).

This compound is stirred with 1 ml 2M ammonium hydroxide and 1 ml methanol under an atmosphere of argon for 5 hours. The mixture is neutralized with dilute hydrochloric acid and worked-up with ether. Chromatography with ether/p-pether 1:10 gives Compound 63.

Preparation 61

Compound 64

Method: General Procedure 3.
Starting material: Compound 12.

Preparation 62

Compound 6

Method: General Procedure 2 (Reaction of Compound II with the side chain building block R—YH (Y=O) (Scheme 1).
Starting material: Compound 5.
R—OH: 3-methylbut-2-en-1-ol.
NMR is identical with the spectrum given in Preparation 4.

Preparation 63

Compound 65

Method: General Procedure 1.
Compound I: Compound 2.
Alkylating agent: 4-(1-ethoxyethoxy)-3,3-difluoro-1-iodo-4-methylpentane (0.6 g).

Preparation 64

Compound 66

Method: General Procedure 3.
Compound I: Compound 65.

General Procedure 4

Conversion of Compounds V to the corresponding Compound I by by desilylation with HF (Examples 1 and 2)

The compound V (ca. 0.2 g) was dissolved in ethyl acetate (0.6 ml) and acetonitrile (8 ml) was added under vigorous stirring. A solution of 5% hydrofluoric acid in acetonitrile/water 8:1 (4.0 ml) was added, and the reaction mixture was stirred under nitrogen at room temperature for 90 minutes. Excess 4N aqueous NaOH solution was added, and the reaction mixture was worked-up (ethyl acetate). The residue was purified by chromatography (ethyl acetate as eluant) to give the compound I.

Example 1

1(S),3(R)-Dihydroxy-20(R)-(3-hydroxy-3-methyl-1-butoxymethyl)-9,10-seco-pregna-5(Z),7(E),10(19)-triene (Compound 102)

Starting material V: Compound 16.
NMR: δ=0.53 (s, 3H), 0.93 (d, 3H, J=6.7), 1.23 (s, 6H), 1.75 (t, 2H), 1.10–2.10 (m, 17H), 2.29 (dd, 1H), 2.57 (dd, 1H), 2.81 (bd, 2H), 3.31 (dd, 1H), 3.42 (dd, 1H), 3.62 (t, 2H), 4.21 (m, 1H), 4.41 (m, 1H), 4.98 (m, 1H), 5.31 (m, 1H), 6.00 (d, 1H, J=11.3), 6.35 (d, 1H, J=11.3).

Example 2

1(S),3(R)-Dihydroxy-20(R)-(4-hydroxy-4-methyl-1-pentyloxymethyl)-9,10-seco-pregna-5(Z),7(E),10(19)-triene (Compound 106)

Starting material V: Compound 17.
NMR: δ=0.53 (s, 3H), 0.92 (d, 3H, J=6.6), 1.20 (s, 6H), 1.10–2.10 (m, 20OH), 2.29 (dd, 1H), 2.57 (m, 2H), 2.81 (m, 1H), 3.17 (dd, 1H), 3.40 (m, 2H), 3.48 (dd, 1H), 4.20 (m, 1H), 4.40 (m, 1H), 4.97 (m, 1H), 5.31 (m, 1H). 6.00 (d, 1H, J=11.2), 6.34 (d, 1H, J=11.2).

General Procedure 5

Conversion of Compounds V to the corresponding Compound I by by desilylation with tetra-n-butylammonium fluoride (Examples 3–6)

A solution of Compound V (0.3 mmol) and tetra-n-butylammonium fluoride trihydrate (1.2 mmol) in THF (10 ml) under N₂ was stirred at 65° C. for 1 hour. The reaction mixture was partitioned between ethyl acetate and 1% sodium hydrogen carbonate solution. Work-up and purification by chromatography (ethyl acetate as eluant) gave title compound I.

Example 3

1(S),3(R)-Dihydroxy-20(R)-(4-hydroxy-4-methyl-1-pent-2-ynyloxymethyl)-9,10-seco-pregna-5(Z),7(E),10(19)-triene (Compound 108)

Starting material V: Compound 21
NMR: δ=0.56 (s, 3H), 0.93 (d, 3H), 1.20–2.05 (m, 17H), 1.50 (s, 6H), 2.30 (dd, 1H), 2.57 (dd, 2H), 2.81 (dd, 1H), 3.21 (dd, 1H), 3.60 (dd, 1H), 4.12 (s, 2H), 4.21 (m, 1H), 4.41 (m, 1H), 4.98 (bs, 1H), 5.31 (bs, 1H), 6.00 (d, 1H), 6.35 (d, 1H).

Example 4

1(S), 3(R)-Dihydroxy-20(R)-(2-hydroxy-2-methyl-1-propyl-thiomethyl)-9,10-seco-pregna-5(Z), 7(E),10(19)-triene (Compound 116)

Starting material V: Compound 18

NMR: δ=0.56 (s, 3H), 1.01 (d, 3H, J=6.6), 1.27 (s, 6H), 1.20–2.10 (m, 16H), 2.31 (dd, 1H), 2.41 (bs, 1H), 2.47 (dd, 1H), 2.60 (dd, 1H), 2.65 (ABq, 2H), 2.83 (m, 2H), 4.22 (m, 1H), 4.42 (m, 1H), 4.99 (m, 1H), 5.33 (m, 1H), 6.02 (d, 1H, J=11.3), 6.37 (d, 1H, J=11.3).

Example 5

1(S),3(R-Dihydroxy-20(R)-(3-hydroxy-3-methyl-1-butylthiomethyl)-9,10-seco-pregna-5(Z),7(E),10(19)-triene (Compound 117)

Starting material V: Compound 19.

NMR: δ=0.56 (s, 3H), 0.99 (d, 3H), 1.24 (s, 6H), 1.3–2.05 (m, 19H), 2.32 (dd, 1H), 2.40 (dd, 1H), 2.60 (m, 3H), 2.82 (m, 2H), 4.23 (m, 1H), 4.42 (m, 1H), 4.99 (bs, 1H), 5.32 (bs, 1H), 6.01 (d, 1H), 6.37 (d, 1H).

Example 6

1(S),3(R)-Dihydroxy-20(R)-(3-hydroxy-3-ethyl-1-pentylthiomethyl)-9,10-seco,pregna-5(Z),7(E),10(19)-triene (Compound 121)

Starting material V: Compound 20.

NMR: δ=0.56 (s, 3H), 0.86 (t, 6H), 0.97 (d, 3H), 1.30–2.05 (m 23H) 2.31 (dd, 1H), 2.40 (dd 1H), 2.55 (m, 3H), 2.82 (m, 2H), 4.21 (m, 1H), 4.41 (m, 1H), 4.99 (bs, 1H), 5.32 (bs, 1H), 6.02 (m, 1H), 6.36 (m, 1H).

Example 7

1(S),3(R)-Dihydroxy-20(R)-(5-hydroxy-5-methyl-1-hexyloxymethyl)-9,10-seco-pregna-5(Z),7(E),10(19)-triene (Compound 126)

Method: General Procedure 4.
Starting material V: Compound 32.
NMR: δ=0.56 (s, 3H), 0.94 (s, 3H), 1.21 (s, 6H), 1.20–2.10 (m, 23H), 2.29 (dd, 1H), 2.59 (dd, 1H), 2.82 (dd, 1H), 3.15 (dd, 1H), 3.41 (m, 2H), 3.48 (dd, 1H), 4.23 (m, 1H), 4.41 (m, 1H), 4.99 (bs, 1H), 5.32 (m, 1H), 6.01 (d, 1H), 6.37 (d, 1H).

Example 8

1(S),3(R)-Dihydroxy-20(R)-[2-(2-hydroxy-2-propyl)-phenoxymethyl]-9,10-seco-pregna-5(Z),7(E),10(19)-triene (Compound 127)

Method: General Procedure 5.
Starting material V: Compound 33.
NMR: δ=0.61 (s, 3H), 1.13 (d, 3H), 1.63 (s, 3H), 1.65 (s, 3H), 1.20–2.20 (m, 16H), 2.31 (dd, 1H), 2.59 (dd, 1H), 2.81 (dd, 1H), 4.03 (m, 2H), 4.22 (m, 1H), 4.44 (m, 1H), 4.48 (s, 1H), 5.00 (m, 1H), 5.33 (m, 1H), 6.03 (d, 1H), 6.36 (d, 1H), 6.89 (dd, 1H), 6.94 (dt, 1H), 7.22 (dt, 1H), 7.31 (dd, 1H).

Example 9

1(S),3(R)-Dihydroxy-20(R)-[2-(3-hydroxy-3-pentyl)-phenoxymethyl]-9,10-seco-pregna-5(Z),7(E),10(19)-triene (Compound 128)

Method: General Procedure 5.
Starting material V: Compound 34.
NMR: δ=0.60 (s, 3H), 0.81 (m, 6H), 1.11 (d, 3H), 1.17–2.20 (m, 20H), 2.31 (dd, 1H), 2.60 (dd, 1H), 2.82 (bd, 1H), 3.98 (m, 2H), 4.10 (bs, 1H), 4.23 (m, 1H), 4.44 (m, 1H), 5.00 (m, 1H), 5.33 (m, 1H), 6.03 (d, 1H), 6.36 (d, 1H), 6.87 (dd, 1H), 6.94 (dt, 1H), 7.21 (dt, 1H), 7.26 (dd, 1H).

Example 10

1(S),3(R)-Dihydroxy-20(R)-[3-(2-hydroxy-2-propyl)-phenoxymethyl]-9,10-seco-pregna-5(Z),7(E),10(19)-triene (Compound 111)

Method: General Procedure 5.
Starting material V: Compound 35.
Compound 111 was crystallized from methyl formate, m.p. 71°–77° C.
UV (EtOH) λ$_{max}$ 266 nm (ε=18672).
NMR: δ=0.60 (s, 3H), 1.06 (d, 3H), 1.57 (s, 6H), 1.20–2.12 (m, 17H), 2.31 (dd, 1H), 2.60 (dd, 1H), 2.82 (bd, 1H), 3.77 (m, 1H), 4.01 (dd, 1H), 4.23 (m, 1H), 4.43 (m, 1H), 5.01 (m, 1H), 5.33 (m, 1H), 6.03 (d, 1H), 6.38 d, 1H), 6.76 (m, 1H), 7.02 (m, 1H), 7.06 (m, 1H), 7.25 (m, 1H).

Example 11

1(S),3(R)-Dihydroxy-20(R)-[3-(3-hydroxy-3-pentyl)-phenoxymethyl]-9,10-seco-pregna-5(Z),7(E),10(19)-triene (Compound 129)

Method: General Procedure 5.
Starting material V: Compound 36.
NMR: δ=0.60 (s, 3H), 0.77 (t, 6H), 1.06 (d, 3H), 1.25–2.10 (m, 21H), 2.31 (dd, 1H), 2.60 (dd, 1H), 2.84 (bd, 1H), 3.75 (dd, 1H), 4.01 (dd, 1H), 4.23 (m, 1H), 4.43 (m, 1H), 5.01 (bs, 1H), 5.33 (bs, 1H), 6.03 (d, 1H), 6.37 (d, 1H), 6.73 (m, 1H), 6.90 (m, 1H), 6.95 (m, 1H), 7.23 (t, 1H).

Example 12

1(S),3(R)-Dihydroxy-20(R)-[4-(2-hydroxy-2-propyl)-phenoxymethyl]-9,10-seco-pregna-5(Z),7(E),10(19)-triene (Compound 130)

Method: General Procedure 5.
Starting material V: Compound 37.
NMR: δ=0.60 (s, 3H), 1.05 (d, 3H), 1.25–2.10 (m, 17H), 1.57 (s, 6H), 2.31 (dd, 1H), 2.60 (dd, 1H), 2.82 (bd, 1H), 3.75 (dd, 1H), 3.99 (dd, 1H), 4.23 (m, 1H), 4.42 (m, 1H), 5.00 (bs, 1H), 5.33 (bs, 1H), 6.03 ( d, 1H), 6.37 ( d, 1H), 6.84 (m, 2H), 7.39 (m, 2H).

Example 13

1(S),3(R)-Dihydroxy-20(R)-[4-(3-hydroxy-3-pentyl)-phenoxymethyl]-9,10-seco-pregna-5(Z),7(E),10(19)-triene (Compound 131)

Method: General Procedure 5.
Starting material V: Compound 38.
Compound 131 was crystallized from methyl formate-hexane, m.p. 131°–136° C.
UV (EtOH) λ$_{max}$ 266 nm (ε=18541).
NMR: δ=0.60 (s, 3H), 0.76 (t, 6H), 1.06 (d, 3H), 1.25–2.10 (m, 21H), 2.31 (dd, 1H), 2.60 (dd, 1H), 2.83

(m, 1H), 3.73 (dd, 1H), 4.00 (dd, 1H), 4.22 (m, 1H), 4.42 (m, 1H), 5.01 (bs, 1H), 5.33 (bs, 1H), 6.03 (d, 1H), 6.37 (d, 1H), 6.85 (m, 2H), 7.26 (m, 2H).

Example 14

1(S),3(R)-Dihydroxy-20(R)-[3-(hydroxymethyl)-phenoxymethyl]-9,10-seco-pregna-5(Z),7(E),10(19)-triene (Compound 132)

Method: General Procedure 4.
Starting material V: Compound 39.

NMR: δ=0.60 (s, 3H), 1.06 (d, 3H), 1.20–2.10 (m, 17H), 2.31 (dd, 1H), 2.59 (dd, 1H), 2.82 (bd, 1H), 3.78 (dd, 1H), 3.99 (dd, 1H), 4.22 (m, 1H), 4.43 (m, 1H), 4.67 (m, 2H), 5.00 (m, 1H), 5.33 (m, 1H), 6.03 (d, 1H), 6.37 (d, 1H), 6.80 (m, 1H), 6.90 (bs, 1H), 6.91 (m, 1H), 7.25 (t, 1H).

Example 15

1(S),3(R)-Dihydroxy-20(R)-(4-hydroxy-4-methyl-1-pent-2(E)-enylohymethyl-9,10-seco-pregna-5(Z),7(E),10(19)-triene (Compound 107)

Method: General Procedure 5.
Starting material V: Compound 40.

NMR: δ=0.54 (s, 3H), 0.94 (d, 3H), 1.31 (s, 6H), 1.15–2.10 (m, 17H), 2.30 (dd, 1H), 2.58 (dd, 1H), 2.81 (dd, 1H), 3.14 (m, 1H), 3.51 (dd, 1H), 3.92 (m, 2H), 4.21 (m, 1H), 4.42 (m, 1H), 4.98 (m, 1H), 5.32 (m, 1H), 5.72 (dt, 1H), 5.84 (d, 1H), 6.00 (d, 1H), 6.35 (d, 1H).

Example 16

1(S),3(R)-Dihydroxy-20(R)-(3-hydroxy-3-ethyl-1-pentyloxymethyl-9,10-seco-pregna-5(Z),7(E),10(19)-triene (Compound 103)

Method: General Procedure 5.
Starting material V: Compound 42.

NMR: δ=0.53 (s, 3H), 0.85 (m, 6H), 0.92 (d, 3H), 1.15–2.15 (m, 22H), 2.28 (dd, 1H), 2.57 (dd, 1H), 2.81 (dd, 1H), 3.29 (dd, 1H), 3.39 (bs, 1H), 3.41 (dd, 1H), 3.58 (t, 2H), 4.20 (m, 1H), 4.40 (m, 1H), 4.97 (m, 1H), 5.30 (m, 1H), 5.99 (d, 1H), 6.35 (d, 1H).

Example 17

1(S),3(R)-Dihydroxy-20(R)-(3-hydroxy-3-ethyl-1-pentylsulphinylmethyl-9,10-seco-pregna-5(Z),7(E),10(19)-triene (Compound 133) (Stereoisomer with Compound 134)

Method: General Procedure 4.
Starting material V: Compound 50.

Compound 133 was purified by chromatography (ethyl acetate/ethanol 10:1 as eluant).

NMR: δ=0.62 (s, 3H), 0.89 (t, 6H), 1.11 (d, 3H), 1.20–2.22 (m, 23H), 2.29 (t, 1H), 2.32 (dd, 1H), 2.60 (dd, 1H), 2.77 (t, 2H), 2.84 (bd, 1H), 3.21 (dd, 1H), 4.23 (m, 1H), 4.43 (m, 1H), 4.99 (m, 1H), 5.33 (m, 1H), 6.03 (d, 1H), 6.36 (d, 1H).

Example 18

1(S),3(R)-Dihydroxy-20(R)-(3-hydroxy-3-ethyl-1-pentylsuphinylmethl-9,10-seco-pregna-5(Z),7(E),10(19)-triene (Compound 134) (Stereoisomer with Compound 133)

Method: General Procedure 4.
Starting material V: Compound 51.

Compound 134 was purified by chromatography (ethyl acetate/ethanol 10:1 as eluant).

NMR: δ=0.58 (s, 3H), 0.88 (dt, 6H), 1.08 (d, 3H), 1.26 (t, 2H), 1.20–2.15 (m, 20H), 2.33 (m, 2H), 2.59 (dd, 1H), 2.69 (m, 2H), 2.84 (m, 2H), 2.99 (dd, 1H), 4.22 (m, 1H), 4.43 (m, 1H), 4.98 (m, 1H), 5.33 (m, 1H), 6.03 (d, 1H), 6.36 (d, 1H).

Example 19

1(S),3(R)-Dihydroxy-20(R)-(3-hydroxy-3-ethyl-1-pentylsulphonylmethyl)-9,10-seco-pregna-5(Z),7(E),10(19)-triene (Compound 135)

Method: General Procedure 4.
Starting material V: Compound 52.

NMR: δ=0.60 (s, 3H), 0.87 (t, 6H), 1.18 (d, 3H), 1.05–2.15 (m, 22H), 2.24 (m, 1H), 2.31 (dd, 1H), 2.59 (dd, 1H), 2.75 (dd, 2H), 2.82 (dd, 1H), 3.05 (m, 2H), 3.31 (dd, 1H), 4.23 (m, 1H), 4.42 (m, 1H), 4.98 (m, 1H), 5.32 (m, 1H), 6.02 (d, 1H), 6.35 (d, 1H).

Example 20

1(S),3(R)-Dihydroxy-20(R)-(4-hydroxy-4-methyl-pentylthiomethyl)-9,10-seco-pregna-5(Z),7(E),10(19)-triene (Compound 136)

Method: General Procedure 5.
Starting material V: Compound 56.

NMR: δ=0.56 (s, 3H), 1.00 (d, 3H), 1.22 (s, 6H), 1.20–2.20 (m, 21H), 2.32 (dd, 1H), 2.37 (dd, 1H), 2.51 (t, 2H), 2.60 (dd, 1H), 2.79 (dd, 1H), 2.83 (bd, 1H), 4.23 (m, 1H), 4.43 (m, 1H), 5.00 (m, 1H), 5.33 (m, 1H), 6.02 (d, 1H), 6.37 (d, 1H).

Example 21

1(S),3(R)-Dihdroxy-20(R)-(3-(hydroxymethyl)phenylthiomethyl)-9,10-seco-pregna-5(Z),7(E), 10(19)-triene (Compound 137)

Method: General Procedure 5.
Starting material V: Compound 58.

NMR: δ=0.53 (s, 3H), 1.04 (d, 3H), 1.15–2.10 (m, 17H), 2.31 (dd, 1H), 2.58 (dd, 1H), 2.76 (dd, 2H), 2.83 (dd, 1H), 3.25 (dd, 1H), 4.22 (m, 1H), 4.41 (m, 1H), 4.66 (s, 2H), 4.99 (m, 1H), 5.32 (m, 1H), 6.01 (d, 1H), 6.36 (d, 1H), 7.14 (m, 1H), 7.25 (m, 2H), 7.33 (s, 1H).

Example 22

1(S),3(R)-Dihydroxy-20(R)-(3-((1-hydroxy-1-methyl)ethyl)phenylthiomethyl)-9,10-seco-pregna-5(Z),7(E),10(19)-triene (Compound 138)

Method: General Procedure 5.
Starting material V: Compound 57.

NMR: δ=0.52 (s, 3H), 1.04 (d, 3H), 1.56 (s, 6H), 1.15–2.10 (m, 17H), 2.31 (dd, 1H), 2.60 (dd, 1H), 2.74 (dd, 1H), 2.83 (dd, 1H), 3.26 (dd, 1H), 4.23 (m, 1H), 4.43 (m, 1H), 4.99 (m, 1H), 5.32 (m, 1H), 6.01 (d, 1H), 6.36 (d, 1H), 7.23 (m, 3H), 7.48 (m, 1H).

Example 23

1(S),3(R)-Dihydroxy-20(R)-(4-hydroxy-4-ethyl-1-hex-2-ynyloxymethyl)-9,10-seco-pregna-5(Z),7(E),10(19)-triene (Compound 139)

Method: General Procedure 5.
Starting material V: Compound 55.

NMR: δ=0.57 (s, 3H), 0.95 (d, 3H), 1.03 (t, 6H), 1.20–2.10 (m, 21H), 2.31 (dd, 1H), 2.60 (dd, 1H), 2.83 (dd, 1H), 3.24 (t, 1H), 3.64 (dd, 1H), 4.17 (ABq, 2H), 4.23 (m, 1H), 4.43 (m, 1H), 4.99 (bs, 1H), 5.33 (bs, 1H), 6.02 (d, 1H), 6.37 (d, 1H).

Example 24

1(S),3(R)-Dihydroxy-20(R)-(2-hydroxyphenoxyme-thyl),9,10-seco-pregna-5(Z),7(E),10(19)-triene (Compound 140)

Method: General Procedure 4.
Starting material V: Compound 61.
Compound 140 was crystallized from methyl formate-hexane, m.p. 125°-130° C.
UV (EtOH) $\lambda_{max}$ 267 nm ($\epsilon$=18691 ). NMR: $\delta((CD_3)_2CO)$=0.63 (s, 3H), 1.10 (d, 3H), 1.25-2.10 (m, 14H), 2.28 (dd, 1H), 2.49 (dd, 1H), 2.84 (m, 1H), 3.65 (d, 1H), 3.90 (d, 1H), 3.92 (dd, 1H ), 4.09 ( dd, 1H), 4.16 (m, 1H), 4.40 (m, 1H), 4.86 (m, 1H), 5.32 (m, 1H), 6.10 (d, 1H), 6.28 (d, 1H), 6.75-7.0 (m, 4H), 7.32 (s, 1H).

Example 25

1(S),3(R)-Dihydroxy-20(R)-(3-hydroxyphenoxyme-thyl)-9,10-seco-pregna-5(Z),7(E),10(19)-triene (Compound 141)

Method: General Procedure 4.
Starting material V: Compound 62.
NMR: $\delta((CD_3)_2CO)$=0.63 (s, 3H), 1.05 (d, 3H), 1.25-2.0 (m, 14H), 2.28 (dd, 1H), 2.49 (dd, 1H), 2.86 (bd, 1H), 3.67 (d, 1H), 3.79 (dd, 1H), 3.92 (d, 1H), 3.98 (dd, 1H), 4.17 (m, 1H), 4.40 (m, 1H), 4.87 (m, 1H), 5.32 (m, 1H), 6.10 (d, 1H), 6.29 (d, 1H), 6.40 (m, 3H), 7.06 (m, 1H), 8.27 (bs, 1H).

Example 26

1(S),3(R)-Dihydroxy-20(R),-(4-hydroxy-4-tri-fluoromethyl-5,5,5-trifluoro-1-pent-2-ynyloxymethyl)-9,10-seco-pregna-5(Z),7(E),10(19)-triene (Compound 109)

Method: General Procedure 5.
Starting material V: Compound 64.

Example 27

1(S),3(R)-Dihydroxy-20(R)-(3,3-difluoro-4-hydroxy-4-methyl-1-pentyloxymethyl)-9,10-seco-pregna-5(Z),7(E),10(19)-triene (Compound 153 )

Method: General Procedure 4.
Starting material V: Compound 66.

Example 28

Capsules containing Compound 106

106 was dissolved in arachis oil to a final concentration of 1 µg 106/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of the 106 in oil solution, such that each capsule contained 0.1 µg 106.

Example 29

Dermatological Cream Containing Compound 106

In 1 g almond oil was dissolved 0.05 mg 106. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of 106 per gram of cream.

What we claim is:

1. A compound of the formula I

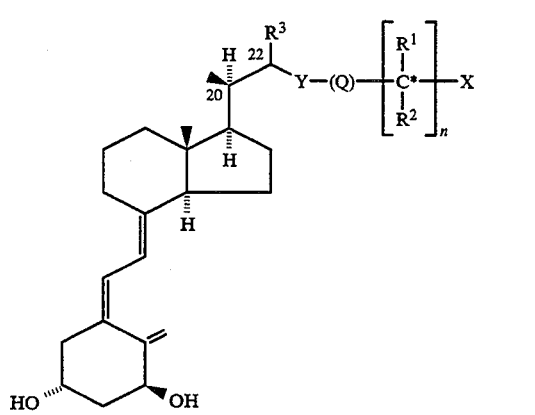

in which formula X is hydrogen or hydroxy; Y is oxygen or sulphur, S(O) or S(O$_2$); R$^1$ and R$^2$, which may be the same or different, stand for hydrogen or C$_1$-C$_6$ hydrocarbyl; or R$^1$ and R$^2$, taken together with the carbon atom, starred in formula I, bearing the group X, can form a C$_3$-C$_8$ carbocyclic ring; Q is a C$_1$-C$_8$ hydrocarbylene diradical; R$^3$ is hydrogen, methyl or ethyl Q may be optionally substituted with one or more fluorine atoms; n is 0 or 1; and derivatives of the compounds of formula I in which one or more hydroxy groups have been transformed into —O-acyl or —O-glycosyl groups, or a phosphate ester, such masked groups being hydrolyzable in vivo.

2. A diastereoisomer of a compound according to claim 1, in pure form; or a mixture of diastereoisomers of a compound according to claim 1.

3. A compound according to claim 1 which is:
   a) 1(S),3(R)-Dihydroxy-20(R)-(4-hydroxy-4-methyl-1-pentyloxymethyl)-9,10-seco-pregna-5(Z),7(E),10(19)-triene
   b) 1(S),3(R)-Dihydroxy-20(R)-(4-hydroxy-4-methyl-1-pent-2-ynyloxymethyl)-9,10-seco-pregna-5(Z),7(E),10(19)-triene
   c) 1(S),3(R) -Dihydroxy-20(R)-(4-hydroxy-4-tri-fluoromethyl-5,5,5-trifluoro-1-pent-2-ynyloxyme-thyl)-9,10-seco-pregna-5(Z),7(E),10(19)-triene
   d) 1(S),3(R)-Dihydroxy-20(R)-[3-(2-hydroxy-2-propyl)phenoxymethyl]-9,10-seco-pregna-5(Z),7(E),10(19)-triene
   e) 1(S),3(R)-Dihydroxy-20(R)-(3-hydroxy-3-ethyl-1-pentylthiomethyl)-9,10-seco-pregna-5(Z),7(E),10(19)-triene
   f) 1(S),3(R)-Dihydroxy-20(R)-(3-hydroxy-3-ethyl-1-pentylsulphonylmethyl)-9,10-seco-pregna-5(Z),7(E),10(19)-triene
   g) 1(S),3(R)-Dihydroxy-20(R)-(3-((1-hydroxy- 1-methyl)ethyl)phenylthiomethyl)-9,10-secopregna-5(Z),7(E),10(10)-triene
   h) 1(S),3(R)-Dihydroxy-20(R)-(3,3-difluoro-4-hydroxy-4-methyl-1-pentyloxymethyl)-9,10-seco-pregna-5(Z),7(E),10(19)-triene.

4. A pharmaceutical composition containing an effective amount of one or more of the compounds of claim 1, together with a pharmaceutically acceptable, non-toxic carrier.

5. A pharmaceutical composition according to claim 4 in dosage unit form.

6. A dosage unit according to claim 5 containing from 0.05-50 µg, of a compound of formula I.

* * * * *

UNITED STATES PATENT AND TRADEMARK OFFICE
CERTIFICATE OF CORRECTION

PATENT NO.    :    5,374,629

DATED         :    December 20, 1994

INVENTOR(S)   :    CALVERLEY et al.

It is certified that error appears in the above-identified patent and that said Letters Patent is hereby corrected as shown below:

Column 1, line 63, change "para), and" to --para).--;

Column 2, line 52, change "1α25" to --1α, 25--;

Column 3, line 45, change "4.3" to --43--.

Columns 11-12, Table 1, compound No. 126, under column heading Q, change "$(CH_2)_2$" to --$(CH_2)_4$--;

Column 18, line 6, following "(bd, 1H)" insert --,--;

Column 18, line 19, delete "D";

Column 18, line 23, change "γ" to --δ--;

Column 30, line 43, change "(m, 20OH)" to --(m, 20H)--;

Column 31, line 19, change "1(S),3(R" to --1(S),3(R)--;

Column 33, line 21, change "enylohymethyl" to --enyloxymethyl--; and

UNITED STATES PATENT AND TRADEMARK OFFICE
CERTIFICATE OF CORRECTION

PATENT NO. : 5,374,629
DATED : December 20, 1994
INVENTOR(S) : Calverley et al.

It is certified that error appears in the above-indentified patent and that said Letters Patent is hereby corrected as shown below:

Column 34, line 33, change "Dihdroxy" to --Dihydroxy--.

Signed and Sealed this

Nineteenth Day of September, 1995

Attest:

BRUCE LEHMAN

Attesting Officer

Commissioner of Patents and Trademarks